United States Patent
Srinivasan et al.

(10) Patent No.: US 10,519,228 B2
(45) Date of Patent: *Dec. 31, 2019

(54) METHODS FOR REDUCING DRUG-INDUCED LIVER INJURY

(71) Applicant: Ten Peaks LLC, Corona Del Mar, CA (US)

(72) Inventors: Sundar Srinivasan, Corona Del Mar, CA (US); Christina Chow, Seattle, WA (US)

(73) Assignee: TEN PEAKS LLC, Corona Del Mar, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/406,700

(22) Filed: May 8, 2019

(65) Prior Publication Data

US 2019/0345243 A1 Nov. 14, 2019

Related U.S. Application Data

(60) Provisional application No. 62/668,388, filed on May 8, 2018.

(51) Int. Cl.
*C07H 21/04* (2006.01)
*C12Q 1/68* (2018.01)
*C07K 16/24* (2006.01)
*C12Q 1/6881* (2018.01)

(52) U.S. Cl.
CPC .......... *C07K 16/241* (2013.01); *C12Q 1/6881* (2013.01); *C07K 2317/24* (2013.01); *C12Q 2600/106* (2013.01)

(58) Field of Classification Search
None
See application file for complete search history.

(56) References Cited

U.S. PATENT DOCUMENTS

| 7,976,838 B2 | 7/2011 | Benyunes |
| 9,624,295 B2 | 4/2017 | Medich et al. |

FOREIGN PATENT DOCUMENTS

| CN | 106282328 A | 1/2017 |

OTHER PUBLICATIONS

Aithal, et al., "Case Definition and Phenotype Standardization in Drug-Induced Liver Injury." Clin Pharmacol Ther. (Jun. 2011); 89(6): 806-815. Epub May 4, 2011.
Carapito, et al., "Next-Generation Sequencing of the HLA locus: Methods and impacts on HLA typing, population genetics and disease association studies." Hum Immunol. (Nov. 2016); 77(11):1016-1023. Epub Apr. 5, 2016.
Nicoletti, et al., "Association of Liver Injury From Specific Drugs, or Groups of Drugs, With Polymorphisms in HLA and Other Genes in a Genome-Wide Association Study." Gastroenterology (Apr. 2017); 152(5): 1078-1089. Epub Dec. 30, 2016.
U.S. Appl. No. 16/406,692, dated May 8, 2019, Pending.
U.S. Appl. No. 16/406,695, dated May 8, 2019, Allowed.
U.S. Appl. No. 16/406,698, dated May 8, 2019, Allowed.
Haroon, et al., "Epidemiology, genetics and management of psoriatic arthritis 2013: focus on developments of who develops the disease, its clinical features, and emerging treatment options", Psoriasis: Targets and Therapy (Apr. 11, 2013); 3: 11-23.
Invitation to Pay Additional Fees for International Application No. PCT/US2019/031318, dated Aug. 2, 2019, 2 pages.
Dougados, et al., "Combination therapy in early rheumatoid arthritis: a randomised, controlled, double blind 52 week clinical trial of sulphasalazine and methotrexate compared with the single components", Ann Rheum Dis (1999); 58(4): 220-225.
Katchamart, et al., "Efficacy and toxicity of methotrexate (MTX) monotherapy versus MTX combination therapy with non-biological disease-modifying antirheumatic drugs in rheumatoid arthritis: a systematic review and meta-analysis", Ann Rheum Dis (2009); 68: 1105-1112.
Mirkin, G., "Why I Prescribe Antibiotics to Patients With Chronic Fatigue Syndrome, Fibromyalgia, Multiple Chemical Sensitivity, and Other Autoimmune Diseases", prohealth.com, Nov. 20, 2002, https://www.prohealth.com/library/why-i-prescribe-antibiotics-to-patients-with-chronic-fatigue-syndrome-fibromyalgia-multiple-chemical-sensitivity-and-other-autoimmune-diseases-20645, downloaded Jul. 24, 2019, 8 pages.
Vercauteren, et al., "A meta-analysis and morphological review of cyclosporine-induced nephrotoxicity in auto-immune diseases", Kidney International (1998); 54(2): 536-545.
French, et al., "Hepatotoxicity Associated with the Use of Anti-TNF-α Agents". Drug Saf. (Mar. 2016); 39(3): 199-208.
International Search Report and Written Opinion for International Application No. PCT/US2019/031318, dated Oct. 9, 2019, 13 pages.
Ortega-Alonso, et al., "Case Characterization, Clinical Features and Risk Factors in Drug-Induced Liver Injury". Int J Mol Sci. (May 2016); 17(5): 714, 22 pages.

*Primary Examiner* — Jeanine A Goldberg
(74) *Attorney, Agent, or Firm* — Cooley LLP

(57) ABSTRACT

The present disclosure provides methods of treating a patient with infliximab or alternative therapies to reduce the risk of developing, and/or severity of, an adverse drug reaction such as drug-induced liver injury. The methods include identifying patients at risk for developing DILI by determining the presence or absence of one or more HLA alleles in the patients.

10 Claims, 5 Drawing Sheets

FIG. 5

Caucasian typed only

| Allele | Presence (11 cases, 60 controls) | | | |
|---|---|---|---|---|
| | Case Count | Control Count | FET | OR |
| HLA-B*39:01 | 3 | 0 | 2.80E-03 | 49.82 |
| HLA-C*12:03 | 4 | 3 | 9.13E-03 | 10.25 |
| HLA-DQB1*02:01 | 5 | 7 | 1.59E-02 | 6.07 |
| HLA-DRB1*03:01 | 5 | 8 | 2.37E-02 | 5.24 |

Caucasian imputed + typed

| Allele | Presence (25 cases, 60 controls) | | | |
|---|---|---|---|---|
| | Case Count | Control Count | FET | OR |
| HLA-DQB1*02:01 | 10 | 7 | 5.96E-03 | 4.93 |
| HLA-B*39:01 | 4 | 0 | 6.25E-03 | 25.33 |
| HLA-DRB1*03:01 | 10 | 8 | 9.37E-03 | 4.24 |
| HLA-C*12:03 | 6 | 3 | 1.08E-02 | 5.85 |
| HLA-DQA1*03:03 | 3 | 0 | 2.33E-02 | 18.82 |
| HLA-C*07:01 | 12 | 14 | 3.78E-02 | 2.99 |

Caucasian imputed only

| Allele | Presence (25 cases, 60 controls) | | | |
|---|---|---|---|---|
| | Case Count | Control Count | FET | OR |
| HLA-DQA1*05:01 | 10 | 7 | 5.96E-03 | 4.93 |
| HLA-DQB1*02:01 | 10 | 7 | 5.96E-03 | 4.93 |
| HLA-B*39:01 | 4 | 0 | 6.25E-03 | 25.33 |
| HLA-DRB1*03:01 | 10 | 8 | 9.37E-03 | 4.24 |
| HLA-DQA1*05:05 | 3 | 21 | 3.65E-02 | 0.26 |
| HLA-C*07:01 | 12 | 14 | 3.78E-02 | 2.99 |

All Ethnicities typed only

| Allele | Presence (14 cases, 66 controls) | | | |
|---|---|---|---|---|
| | Case Count | Control Count | FET | OR |
| HLA-B*39:01 | 3 | 0 | 4.43E-03 | 40.48 |
| HLA-C*12:03 | 4 | 3 | 1.58E-02 | 8.05 |
| HLA-DQB1*02:01 | 5 | 7 | 3.10E-02 | 4.56 |
| HLA-DRB1*03:01 | 5 | 8 | 4.50E-02 | 3.94 |

All ethnicities imputed + typed

| Allele | Presence (31 cases, 66 controls) | | | |
|---|---|---|---|---|
| | Case Count | Control Count | FET | OR |
| HLA-DQB1*02:01 | 12 | 7 | 2.13E-03 | 5.21 |
| HLA-DRB1*03:01 | 12 | 8 | 5.78E-03 | 4.50 |
| HLA-B*39:01 | 4 | 0 | 9.08E-03 | 21.76 |
| HLA-C*12:03 | 6 | 3 | 2.79E-02 | 4.94 |
| HLA-DQA1*03:01 | 4 | 23 | 2.93E-02 | 0.28 |
| HLA-DQA1*03:03 | 3 | 0 | 3.05E-02 | 16.33 |
| HLA-C*07:01 | 14 | 15 | 3.28E-02 | 2.77 |

All ethnicities imputed only

| Allele | Presence (31 cases, 66 controls) | | | |
|---|---|---|---|---|
| | Case Count | Control Count | FET | OR |
| HLA-DQB1*02:01 | 13 | 7 | 8.33E-04 | 5.95 |
| HLA-DQA1*05:01 | 12 | 8 | 5.78E-03 | 4.50 |
| HLA-DRB1*03:01 | 12 | 8 | 5.78E-03 | 4.50 |
| HLA-B*39:01 | 4 | 0 | 9.08E-03 | 21.76 |
| HLA-C*07:01 | 14 | 15 | 3.28E-02 | 2.77 |

African typed only

| Allele | Presence (3 cases, 6 controls) | | | |
|---|---|---|---|---|
| | Case Count | Control Count | FET | OR |
| HLA-A*02:01 | 3 | 0 | 1.19E-02 | 91.00 |
| HLA-DPB1*04:02 | 3 | 1 | 4.76E-02 | 25.67 |

African imputed + typed

| Allele | Presence (3 cases, 6 controls) | | | |
|---|---|---|---|---|
| | Case Count | Control Count | FET | OR |
| HLA-A*02:01 | 3 | 0 | 1.19E-02 | 91.00 |
| HLA-DPB1*04:02 | 3 | 1 | 4.76E-02 | 25.67 |

African imputed only

| Allele | Presence (3 cases, 6 controls) | | | |
|---|---|---|---|---|
| | Case Count | Control Count | FET | OR |
| HLA-A*02:01 | 3 | 0 | 1.19E-02 | 91.00 |

METHODS FOR REDUCING DRUG-INDUCED LIVER INJURY

CROSS-REFERENCE TO RELATED APPLICATIONS

This application claims priority to U.S. Provisional Application No. 62/663,388, filed May 8, 2018, Which is incorporated herein by reference in its entirety for all purposes.

BACKGROUND

Adverse drug reactions (ADRs) can occur in patients who are treated with therapeutic agents. In particular, drug-induced liver injury (DILI) is a serious ADR that can lead to acute liver failure. Upon diagnosis of DILI, administration of the therapeutic drug that triggered the DILI is generally either reduced or discontinued, but often DILI is not detected early enough to avoid long-term or permanent liver damage, or even death.

Infliximab is a monoclonal antibody that inhibits tumor necrosis factor (TNF), a cytokine that is involved in inflammatory processes such as those that occur in autoimmune diseases. Infliximab is approved by the United States Food and Drug Administration (FDA) for the treatment of various autoimmune disorders including rheumatoid arthritis, Crohn's disease, ulcerative colitis, ankylosing spondylitis, psoriatic arthritis, and plaque psoriasis; and is under investigation as a potential therapeutic agent for various other indications, including autoimmune disorders and diseases and conditions that are not autoimmune disorders.

Infliximab has been linked to many instances of liver injury, but there is no information currently available to help assess a patient population's risk of developing DILI. There is a need in the art to predict, manage, and prevent the development of dangerous ADRs such as DILI in patients that have been or may otherwise be prescribed infliximab. This disclosure addresses this and other needs.

SUMMARY OF THE INVENTION

The present disclosure provides for methods of treating a subject or patient population suffering from an autoimmune, inflammatory, or other disease that may be amenable to treatment with infliximab, while reducing the risk and/or severity of drug-induced liver injury (DILI). The present inventors found that the presence of particular HLA alleles, or sets of alleles, in a subject confers to the subject a higher risk of the development of DILI upon administration of infliximab. Accordingly, the methods provided herein involve identifying the at-risk subject or patient population, and reducing the risk of development and/or reducing the severity of DILI in the subject or patient population.

In one aspect, the present disclosure provides methods for treating an autoimmune disease in a subject in need thereof. In another aspect, the present disclosure provides methods for reducing the risk of drug-induced liver injury (DILI) in a subject while treating the subject for an autoimmune disease. In some embodiments, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof. In certain embodiments, the subject has an HLA profile comprising HLA-B*39:01. In some embodiments, the methods comprise administering to the subject a therapeutic agent for the treatment of the autoimmune disease that is not infliximab. In some embodiments, the therapeutic agent for the treatment of the autoimmune disease that is not infliximab is selected from the group consisting of azathioprine, mercaptopurine, adalimumab, certolizumab, methotrexate, natalizumab, vedolizumab, ustekinumab, mesalamine, budesonide, hyoscyamine, celecoxib, hydroxychloroquin, etanercept, prednisone, cyclosporine, tocilizumab, meloxicam, leflunomide, sulfasalazine, abatacept, rituximab, golimumab, acitretin, secukinumab, apremilast, sarilumab, ixekizumab, and corticotropin. In particular embodiments, the therapeutic agent for the treatment of the autoimmune disease that is not infliximab is selected from the group consisting of adalimumab, certolizumab, natalizumab, ustekinumab, vedolizumab, azathioprine, cyclosporine, methotrexate, mercaptopurin, etanercept, and rituximab.

In some embodiments, the methods provided herein comprise or are related to treating a subject having an autoimmune disease, wherein the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof. In some embodiments, the autoimmune disease is selected from the group consisting of Crohn's disease, ulcerative colitis, rheumatoid arthritis, ankylosing spondylitis, psoriatic arthritis, and plaque psoriasis.

In further embodiments, the autoimmune disease is rheumatoid arthritis, ankylosing spondylitis, or psoriatic arthritis; and the therapeutic agent for the treatment of the autoimmune disease that is not infliximab is selected from the group consisting of methotrexate, abatacept, adalimumab, rituximab, etanercept, certolizumab, and golimumab. In other embodiments, the autoimmune disease is Crohn's disease or ulcerative colitis, and the therapeutic agent for the treatment of the autoimmune disease that is not infliximab is selected from the group consisting of adalimumab, certolizumab, natalizumab, ustekinumab, vedolizumab, azathioprine, cyclosporine, methotrexate, and mercaptopurin.

In one aspect, the present disclosure provides methods for treating a condition in a subject in need of infliximab therapy, comprising: administering a therapeutically effective amount of infliximab to the subject, wherein the subject has a decreased risk of drug-induced liver injury (DILI), wherein the subject's decreased risk of DILI is associated with an absence of one or more genetic variations in the subject, wherein the subject has been tested for a presence of the one or more genetic variations with a genetic assay and has been identified as not having the one or more genetic variations, wherein the genetic variation comprises at least one HLA allele selected from the group consisting of HLA-B*39:01, HLA-C*12:03, HLA-DQA1*03:01, HLA-DPB1*04:02, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:

01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof. In some embodiments, the genetic variation comprises the HLA-B*39:01 allele. In some embodiments, the genetic assay comprises one or more of a polymerase chain reaction (PCR)-based approach, a direct sequencing approach, a next generation (NGS) approach and/or a direct HLA typing test. In some embodiments, the genetic assay comprises obtaining a PCR-amplified genomic DNA sample of the biological sample from the subject, contacting under hybridizing conditions the genomic DNA with an oligonucleotide that specifically hybridizes to HLA-B*039:01, and detecting the presence or absence of HLA-B*039:01 in the sample. In some embodiments, the method comprises obtaining a biological sample from the subject and performing the genetic assay on the biological sample.

In one aspect, the present disclosure provides methods for treating a subject with infliximab, wherein the subject is in need of treatment for an autoimmune disease, the method comprising the steps of: (i) determining the subject's risk of developing DILI upon treatment with infliximab by obtaining or having obtained the HLA profile of the subject; and (ii) if the subject has a defined HLA profile, then administering infliximab to the subject in an amount of less than 5 mg/kg, and if the subject does not have the HLA profile, then administering infliximab to the subject in an amount of 5 mg/kg or more. In some embodiments, the risk of DILI in a subject having the defined HLA profile is lower following administration of less than 5 mg/kg infliximab than it would be if the infliximab was administered in an amount of 5 mg/kg infliximab or more. In some embodiments, the defined HLA profile comprises at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof. In some embodiments, the methods comprise administering infliximab to the subject in an amount of less than about 5 mg/kg, less than about 4.5 mg/kg, less than about 4 mg/kg, less than about 3.5 mg/kg, less than about 3 mg/kg, less than about 2.5 mg/kg, less than about 2 mg/kg, less than about 1.5 mg/kg, less than about 1 mg/kg, less than about 0.5 mg/kg, less than about 0.25 mg/kg, less than about 0.1 mg/kg, or less if the subject has the defined HLA profile. In some embodiments, the methods comprise administering 0 mg/kg infliximab to the subject if the subject has the defined HLA profile. In some embodiments, the method comprises administering infliximab in an amount of 5 mg/kg or more if the subject does not have the defined HLA profile. In some embodiments, the risk of DILI in the subject having the defined HLA profile is lower following administration of less than about 5 mg/kg, less than about 4.5 mg/kg, less than about 4 mg/kg, less than about 3.5 mg/kg, less than about 3 mg/kg, less than about 2.5 mg/kg, less than about 2 mg/kg, less than about 1.5 mg/kg, less than about 1 mg/kg, less than about 0.5 mg/kg, less than about 0.25 mg/kg, less than about 0.1 mg/kg, or less of infliximab. In some embodiments, administration of 0 mg/kg infliximab to the subject having an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, reduces the risk of development of DILI in the subject to the level of risk of a subject who does not have an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof.

In one aspect, the present disclosure provides methods for treating an autoimmune disease in a subject in need thereof, the method comprising (i) determining if the subject has a defined HLA profile, and (ii) administering infliximab to the subject in an amount of less than 5 mg/kg if the subject has the defined HLA profile. In some embodiments, the defined HLA profile comprises at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof. In some embodiments, the methods comprise determining if the subject has the defined HLA profile; and administering infliximab to the subject in an amount of less than about 5 mg/kg, less than about 4.5 mg/kg, less than about 4 mg/kg, less than about 3.5 mg/kg, less than about 3 mg/kg, less than about 2.5 mg/kg, less than about 2 mg/kg, less than about 1.5 mg/kg, less than about 1 mg/kg, less than about 0.5 mg/kg, less than about 0.25 mg/kg, less than about 0.1 mg/kg, or less if the subject has the defined HLA profile, and administering infliximab in an amount of 5 mg/kg or more if the subject does not have the defined HLA profile. In such embodiments, the risk of DILI in the subject having the defined HLA profile is lower following administration of less than about 5 mg/kg, less than about 4.5 mg/kg, less than about 4 mg/kg, less than about 3.5 mg/kg, less than about 3 mg/kg, less than about 2.5 mg/kg, less than about 2 mg/kg, less than about 1.5 mg/kg, less than about 1 mg/kg, less than about 0.5 mg/kg, less than about 0.25 mg/kg, less than about 0.1 mg/kg, or less of infliximab.

In one aspect, the present disclosure provides methods for treating an autoimmune disease in a subject in need thereof, wherein the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and wherein the method comprises administering to the subject infliximab at a dose of less than 5 mg/kg body weight of infliximab. In further embodiments, the method comprises administering to the subject infliximab at a dose of less than about 5 mg/kg, less than about 4.5 mg/kg, less than about 4 mg/kg, less than about 3.5 mg/kg, less than about 3 mg/kg, less than about 2.5 mg/kg, less than about 2 mg/kg, less than about 1.5 mg/kg, less than about 1 mg/kg, less than about 0.5 mg/kg, less than about 0.25 mg/kg, less than about 0.1 mg/kg, or less. In yet further embodiments, the method comprises administering to the subject 0 mg/kg infliximab.

In one aspect, the present disclosure provides methods for treating a subject selected for treatment with infliximab, wherein the subject is in need of treatment for an autoimmune disease, wherein the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof. In some embodiments, the method comprises administering to the subject infliximab at a dose of less than 5 mg/kg body weight of infliximab. In further embodiments, the method comprises administering to the subject infliximab at a dose of less than about 5 mg/kg, less than about 4.5 mg/kg, less than about 4 mg/kg, less than about 3.5 mg/kg, less than about 3 mg/kg, less than about 2.5 mg/kg, less than about 2 mg/kg, less than about 1.5 mg/kg, less than about 1 mg/kg, less than about 0.5 mg/kg, less than about 0.25 mg/kg, less than about 0.1 mg/kg, or less. In further embodiments, the method comprises administering to the subject 0 mg/kg infliximab.

In some embodiments, the present disclosure provides methods for treating a subject selected for treatment with infliximab, wherein the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and wherein the method comprises administering infliximab to a subject having the HLA profile in an amount of less than 5 mg/kg and further comprising administering to the subject an additional therapeutic agent. In further embodiments, the method comprises administering to the subject infliximab at a dose of less than about 5 mg/kg, less than about 4.5 mg/kg, less than about 4 mg/kg, less than about 3.5 mg/kg, less than about 3 mg/kg, less than about 2.5 mg/kg, less than about 2 mg/kg, less than about 1.5 mg/kg, less than about 1 mg/kg, less than about 0.5 mg/kg, less than about 0.25 mg/kg, less than about 0.1 mg/kg, or less, and an additional therapeutic agent. In further embodiments, the method comprises administering to the subject 0 mg/kg infliximab and an additional therapeutic agent. In some embodiments, the additional therapeutic agent is selected from the group consisting of azathioprine, mercaptopurine, adalimumab, certolizumab, methotrexate, natalizumab, vedolizumab, ustekinumab, mesalamine, budesonide, hyoscyamine, celecoxib, hydroxychloroquin, etanercept, prednisone, cyclosporine, tocilizumab, meloxicam, leflunomide, sulfasalazine, abatacept, rituximab, golimumab, acitretin, secukinumab, apremilast, sarilumab, ixekizumab, and corticotropin. In particular embodiments, the additional therapeutic agent is selected from the group consisting of adalimumab, certolizumab, natalizumab, ustekinumab, vedolizumab, azathioprine, cyclosporine, methotrexate, mercaptopurin, etanercept, and rituximab. In some embodiments, the additional therapeutic agent is a TNF inhibitor that is not infliximab.

In some embodiments, the subject has rheumatoid arthritis, ankylosing spondylitis, or psoriatic arthritis, and the additional therapeutic agent is selected from the group consisting of methotrexate, abatacept, adalimumab, rituximab, etanercept, certolizumab, and golimumab. In other embodiments, the subject has Crohn's disease or ulcerative colitis, and the additional therapeutic agent is selected from the group consisting of adalimumab, certolizumab, natalizumab, ustekinumab, vedolizumab, azathioprine, cyclosporine, methotrexate, and mercaptopurin.

In one aspect, the present disclosure provides methods for treating an autoimmune disease in a subject selected for infliximab treatment, wherein the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and wherein the subject is treated by reducing the dose of infliximab to 0 mg/kg. In some embodiments, the method reduces the risk of DILI in the subject. In some embodiments, the method treats or prevents DILI in the subject.

In one aspect, the present disclosure provides methods for treating a subject for an autoimmune disease, wherein the subject was selected for infliximab treatment, wherein the method comprises removing administration of infliximab from the subject's treatment regimen, wherein the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof. In some embodiments, the method reduces the risk of DILI in the subject. In some embodiments, the method treats or prevents DILI in the subject.

In various embodiments provided herein, the present disclosure provides methods for treating an autoimmune disease in a subject selected for infliximab treatment and methods for treating a subject for an autoimmune disease wherein the subject was selected for infliximab treatment, wherein the method comprises reducing the dose of infliximab to 0 mg/kg and/or wherein the method comprises removing administration of infliximab from the subject's treatment regimen, wherein the method further comprises administering to the subject a treatment selected from the group consisting of azathioprine, mercaptopurine, adalimumab, certolizumab, methotrexate, natalizumab, vedolizumab, ustekinumab, mesalamine, budesonide, hyoscyamine, celecoxib, hydroxychloroquin, etanercept, prednisone, cyclosporine, tocilizumab, meloxicam, leflunomide, sulfasalazine, abatacept, rituximab, golimumab, acitretin, secukinumab, apremilast, sarilumab, ixekizumab, and corticotropin. In other embodiments, the method further comprises administering to the subject a TNF inhibitor that is not infliximab.

In one aspect, the present disclosure provides methods for treating an autoimmune disease in a subject in need thereof, wherein the subject was administered infliximab and has exhibited symptoms of liver injury. In some embodiments, the method comprises ceasing administration of infliximab, obtaining or having obtained the HLA profile of the subject, and selecting the subject for treatment with a therapeutic agent that is an alternative to infliximab if the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof. In further embodiments, the alternative to infliximab is selected from the group consisting of azathioprine, mercaptopurine, adalimumab, certolizumab, methotrexate, natalizumab, vedolizumab, ustekinumab, mesalamine, budesonide, hyoscyamine, celecoxib, hydroxychloroquin, etanercept, prednisone, cyclosporine, tocilizumab, meloxicam, leflunomide, sulfasalazine, abatacept, rituximab, golimumab, acitretin, secukinumab, apremilast, sarilumab, and corticotropin. In some embodiments, the alternative to infliximab is a TNF inhibitor that is not infliximab. In some embodiments, the method further comprises administering to the subject an anti-inflammatory drug. For example, in some embodiments, the method comprises administering a steroid to the subject.

In one aspect, the present disclosure provides methods for treating an autoimmune disease in a subject in need thereof, wherein the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and wherein the subject is treated using an active regimen comprising: (i) monitoring the subject for liver injury, and (ii) not administering infliximab to the subject. In further embodiments, the active regimen comprising monitoring for liver injury comprises one or more of monitoring liver enzyme levels, monitoring serum bilirubin levels, monitoring the subject for jaundice, and monitoring the subject for upper abdominal discomfort. In some embodiments, the subject is monitored for liver injury daily, every other day, every two days, twice per week, weekly, every two weeks, or monthly.

In various aspects of the present disclosure, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof. Thus, the disclosure is related to a particular patient population having at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof. In further embodiments, the HLA profile of the subject and/or patient population comprises a combination of two of the HLA alleles, or a combination of three of the HLA alleles, or a combination of four of the HLA alleles, or a combination of five or more of the HLA alleles.

In one aspect, the present disclosure provides a method for treating patients having an autoimmune disease with infliximab, wherein the population excludes patients having an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof. Thus, in some embodiments, the present disclosure provides a method of treating a population of patients having an autoimmune disease with infliximab, wherein the method comprises excluding patients having an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, from the population of patients; and treating the population of patients with at least 1 mg/kg, at least 2 mg/kg, at least 3 mg/kg, at least 4 mg/kg, or at least 5 mg/kg infliximab.

In one aspect, the present disclosure provides methods for treating an autoimmune disease in a subject in need thereof, wherein the subject has been determined to have an HLA profile that does not include any HLA allele selected from the group consisting of HLA-B*39:01, HLA-C*12:03, HLA-DQA1*03:01, HLA-DPB1*04:02, HLA-DQA1*03:03, HLA-DQA1*02:01, HLA-DRB1*07:01, HLA-DQB1*02:02, HLA-B*13:02, HLA-A*01:01, HLA-A*24:02, HLA-C*06:02, HLA-B*40:01, HLA-DPB1*04:01, HLA-DQB1*03:03, HLA-C*02:02, HLA-C*03:04, HLA-DRB1*11:01, HLA-DQA1*05:05, HLA-DQB1*02:01, HLA-DQA1*05:01, HLA-DRB1*03:01, HLA-A*02:01, HLA-DQB1*03:01, HLA-A*03:01, HLA-DPB1*04:02, HLA-C*07:01, HLA-B*44:03, and HLA-C*05:01, wherein the method comprises administering infliximab to the subject.

In one aspect, the present disclosure provides methods for treating an autoimmune disease in a subject in need thereof, the method comprising: (i) detecting whether the subject has an HLA profile that includes one or more HLA alleles selected from the group consisting of HLA-B*39:01, HLA-C*12:03, HLA-DQA1*03:01, HLA-DPB1*04:02, HLA-DQA1*03:03, HLA-DQA1*02:01, HLA-DRB1*07:01, HLA-DQB1*02:02, HLA-B*13:02, HLA-A*01:01, HLA-A*24:02, HLA-C*06:02, HLA-B*40:01, HLA-DPB1*04:01, HLA-DQB1*03:03, HLA-C*02:02, HLA-C*03:04, HLA-DRB1*11:01, HLA-DQA1*05:05, HLA-DQB1*02:01, HLA-DQA1*05:01, HLA-DRB1*03:01, HLA-A*02:01, HLA-DQB1*03:01, HLA-A*03:01, HLA-DPB1*04:02, HLA-C*07:01, HLA-B*44:03, and HLA-C*05:01; and (ii) administering infliximab to the subject. In further embodiments, the methods comprise obtaining a biological sample from the subject prior to detecting the HLA profile of the subject. In further embodiments, the methods comprise determining that the subject does not have one or more HLA alleles selected from the group consisting of HLA-B*39:01, HLA-C*12:03, HLA-DQA1*03:01, HLA-DPB1*04:02, HLA-DQA1*03:03, HLA-DQA1*02:01, HLA-DRB1*07:01, HLA-DQB1*02:02, HLA-B*13:02, HLA-A*01:01, HLA-A*24:02, HLA-C*06:02, HLA-B*40:01, HLA-DPB1*04:01, HLA-DQB1*03:03, HLA-C*02:02, HLA-C*03:04, HLA-DRB1*11:01, HLA-DQA1*05:05, HLA-DQB1*02:01, HLA-DQA1*05:01, HLA-DRB1*03:01, HLA-A*02:01, HLA-DQB1*03:01, HLA-A*03:01, HLA-DPB1*04:02, HLA-C*07:01, HLA-B*44:03, and HLA-C*05:01. Thus, in some embodiments, the present disclosure provides methods for treating an autoimmune disease in a subject in need thereof, comprising: (i) obtaining a biological sample from the subject; (ii) detecting whether the subject has an HLA profile that includes one or more HLA alleles selected from the group consisting of HLA-B*39:01, HLA-C*12:03, HLA-DQA1*03:01, HLA-DPB1*04:02, HLA-DQA1*03:03, HLA-DQA1*02:01, HLA-DRB1*07:01, HLA-DQB1*02:02, HLA-B*13:02, HLA-A*01:01, HLA-A*24:02, HLA-C*06:02, HLA-B*40:01, HLA-DPB1*04:01, HLA-DQB1*03:03, HLA-C*02:02, HLA-C*03:04, HLA-DRB1*11:01, HLA-DQA1*05:05, HLA-DQB1*02:01, HLA-DQA1*05:01, HLA-DRB1*03:01, HLA-A*02:01, HLA-DQB1*03:01, HLA-A*03:01, HLA-DPB1*04:02, HLA-C*07:01, HLA-B*44:03, and HLA-C*05:01; (iii) determining that the subject does not have one or more HLA alleles selected from the group consisting of HLA-B*39:01, HLA-C*12:03, HLA-DQA1*03:01, HLA-DPB1*04:02, HLA-DQA1*03:03, HLA-DQA1*02:01, HLA-DRB1*07:01, HLA-DQB1*02:02, HLA-B*13:02, HLA-A*01:01, HLA-A*24:02, HLA-C*06:02, HLA-B*40:01, HLA-DPB1*04:01, HLA-DQB1*03:03, HLA-C*02:02, HLA-C*03:04, HLA-DRB1*11:01, HLA-DQA1*05:05, HLA-DQB1*02:01, HLA-DQA1*05:01, HLA-DRB1*03:01, HLA-A*02:01, HLA-DQB1*03:01, HLA-A*03:01, HLA-DPB1*04:02, HLA-C*07:01, HLA-B*44:03, and HLA-C*05:01, based on detecting the absence of said HLA alleles in step (ii); (iv) administering infliximab to the subject.

In some embodiments, the HLA profiles provided herein comprise at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, and HLA-C*03:03, or any combination thereof.

In further embodiments, the HLA profiles provided herein comprise at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof.

In some embodiments, the HLA profile of the subject and/or patient population comprises HLA-B*39:01.

In some embodiments, the HLA profile of the subject and/or patient population comprises a combination of two HLA alleles, wherein the 2-allele combination is selected from the group consisting of:

HLA-B*07:02, HLA-DQA1*01:03,
HLA-C*07:02, HLA-DQA1*01:03,
HLA-A*24:02, HLA-DQA1*01:03,
HLA-DQA1*03:03, HLA-DRB1*13:01,
HLA-DQA1*03:03, HLA-DQB1*06:03,
HLA-DQA1*01:03, HLA-DQA1*03:03,
HLA-DPB1*01:01, HLA-DQB1*02:01,
HLA-DPB1*01:01, HLA-DQA1*05:01, and
HLA-DPB1*01:01, HLA-DRB1*03:01.

In other embodiments, the HLA profile of the subject and/or patient population comprises a combination of three HLA alleles, wherein the 3-allele combination is selected from the group consisting of:

HLA-A*24:02, HLA-DQA1*01:03, HLA-DQA1*03:03,
HLA-A*24:02, HLA-DQA1*03:03, HLA-DQB1*06:03,
HLA-A*24:02, HLA-DQA1*03:03, HLA-DRB1*13:01,
HLA-A*24:02, HLA-B*07:02, HLA-DQA1*01:03,
HLA-B*07:02, HLA-DPB1*04:01, HLA-DQA1*01:03,
HLA-A*24:02, HLA-DPB1*04:01, HLA-DQA1*01:03,
HLA-C*07:02, HLA-DPB1*04:01, HLA-DQA1*01:03,
HLA-A*24:02, HLA-DQB1*03:01, HLA-DQB1*06:03,
HLA-A*24:02, HLA-DQB1*03:01, HLA-DRB1*13:01,
HLA-A*24:02, HLA-C*07:02, HLA-DQA1*01:03,
HLA-A*24:02, HLA-DQA1*01:03, HLA-DQB1*03:01,
HLA-B*07:02, HLA-C*07:02, HLA-DQA1*01:03,
HLA-DPB1*04:01, HLA-DQA1*01:03, HLA-DQA1*03:03,
HLA-DPB1*04:01, HLA-DQA1*03:03, HLA-DRB1*13:01,
HLA-DPB1*04:01, HLA-DQA1*03:03, HLA-DQB1*06:03,
HLA-A*02:01, HLA-C*03:03, HLA-DQA1*05:01,
HLA-A*02:01, HLA-C*03:03, HLA-DQB1*02:01,
HLA-A*02:01, HLA-C*03:03, HLA-DRB1*03:01,
HLA-A*02:01, HLA-A*24:02, HLA-DQA1*01:03,
HLA-DQA1*03:03, HLA-DQB1*03:01, HLA-DRB1*13:01,
HLA-A*02:01, HLA-DPB1*01:01, HLA-DQB1*02:01,
HLA-DQA1*01:03, HLA-DQA1*03:03, HLA-DQB1*03:01,
HLA-DQA1*03:03, HLA-DQB1*03:01, HLA-DQB1*06:03,
HLA-A*02:01, HLA-DPB1*01:01, HLA-DQA1*05:01, and
HLA-A*02:01, HLA-DPB1*01:01, HLA-DRB1*03:01.

In still other embodiments, the HLA profile of the subject and/or patient population comprises a combination of three HLA alleles, wherein the 3-allele combination is selected from the group consisting of:

HLA-A*24:02, HLA-DPB1*04:01, HLA-DQA1*01:03, HLA-DQA1*03:03,

HLA-A*24:02, HLA-DPB1*04:01, HLA-DQA1*03:03, HLA-DQB1*06:03,

HLA-A*24:02, HLA-DPB1*04:01, HLA-DQA1*03:03, HLA-DRB1*13:01,

HLA-A*24:02, HLA-DQA1*01:03, HLA-DQA1*03:03, HLA-DQB1*03:01,

HLA-A*24:02, HLA-DQA1*03:03, HLA-DQB1*03:01, HLA-DQB1*06:03,

HLA-A*24:02, HLA-DQA1*03:03, HLA-DQB1*03:01, HLA-DRB1*13:01,

HLA-A*24:02, HLA-DQA1*01:03, HLA-DQA1*03:03, HLA-DQB1*06:03,

HLA-A*24:02, HLA-DQA1*01:03, HLA-DQA1*03:03, HLA-DRB1*13:01,

HLA-A*24:02, HLA-DQA1*03:03, HLA-DQB1*06:03, HLA-DRB1*13:01, and

HLA-A*24:02, HLA-B*07:02, HLA-DPB1*04:01, HLA-DQA1*01:03.

In some embodiments, the HLA profile of the subject and/or patient population comprises a combination of the following HLA alleles: HLA-C*07:01, HLA-DQA1*05:01, HLA-DQB1*02:01, HLA-DRB1*03:01, HLA-B*08:01, and HLA-DPB1*01:01.

In some embodiments, the HLA profile of the subject and/or patient population comprises a combination of the following HLA alleles: HLA-DPB1*04:01, HLA-DQA1*01:03, HLA-DQB1*03:01, HLA-DQA1*03:03, HLA-DQB1*06:03, HLA-DRB1*13:01, and HLA-DRB1*04:01.

In some embodiments, the HLA profile of the subject and/or patient population comprises a combination of the following HLA alleles HLA-DPB1*04:01, HLA-C*07:01, HLA-DQA1*05:01, HLA-DQB1*02:01, HLA-DRB1*03:01, HLA-A*01:01, HLA-B*08:01, and HLA-DPB1*01:01.

Accordingly, in some embodiments, the present disclosure provides methods for identifying and treating a particular patient population as defined herein. In some embodiments, the patient population is a population of subjects having the HLA profile provided herein, and suffering from an autoimmune disease. In some embodiments, the patient population is a population of subjects having the HLA profile provided herein, and suffers from an inflammatory disease. In some embodiments, the patient population is a population of subjects having the HLA profile provided herein, and suffering from a disease or disorder for which infliximab may be administered as a therapeutic agent. In some embodiments, the patient population is a population of subjects who do not have the HLA profile provided herein. In some embodiments, the population of patients is a population from which patients having the HLA profile provided herein have been excluded.

In some embodiments, the HLA profile is or has been obtained using a polymerase chain reaction (PCR)-based approach. In some embodiments, the HLA profile is or has been obtained by obtaining a PCR-amplified genomic DNA sample of a biological sample from the subject, contacting under hybridizing conditions the genomic DNA with an oligonucleotide that specifically hybridizes to at least one HLA allele of claim 1, and detecting the presence of at least one HLA allele. In some embodiments, the HLA profile is or has been obtained using next-generation sequencing of the HLA locus.

BRIEF DESCRIPTION OF THE FIGURES

FIG. 5 shows a summary of the alleles with significant results in the cases vs. controls individual data sets.

DETAILED DESCRIPTION

Figure 1:
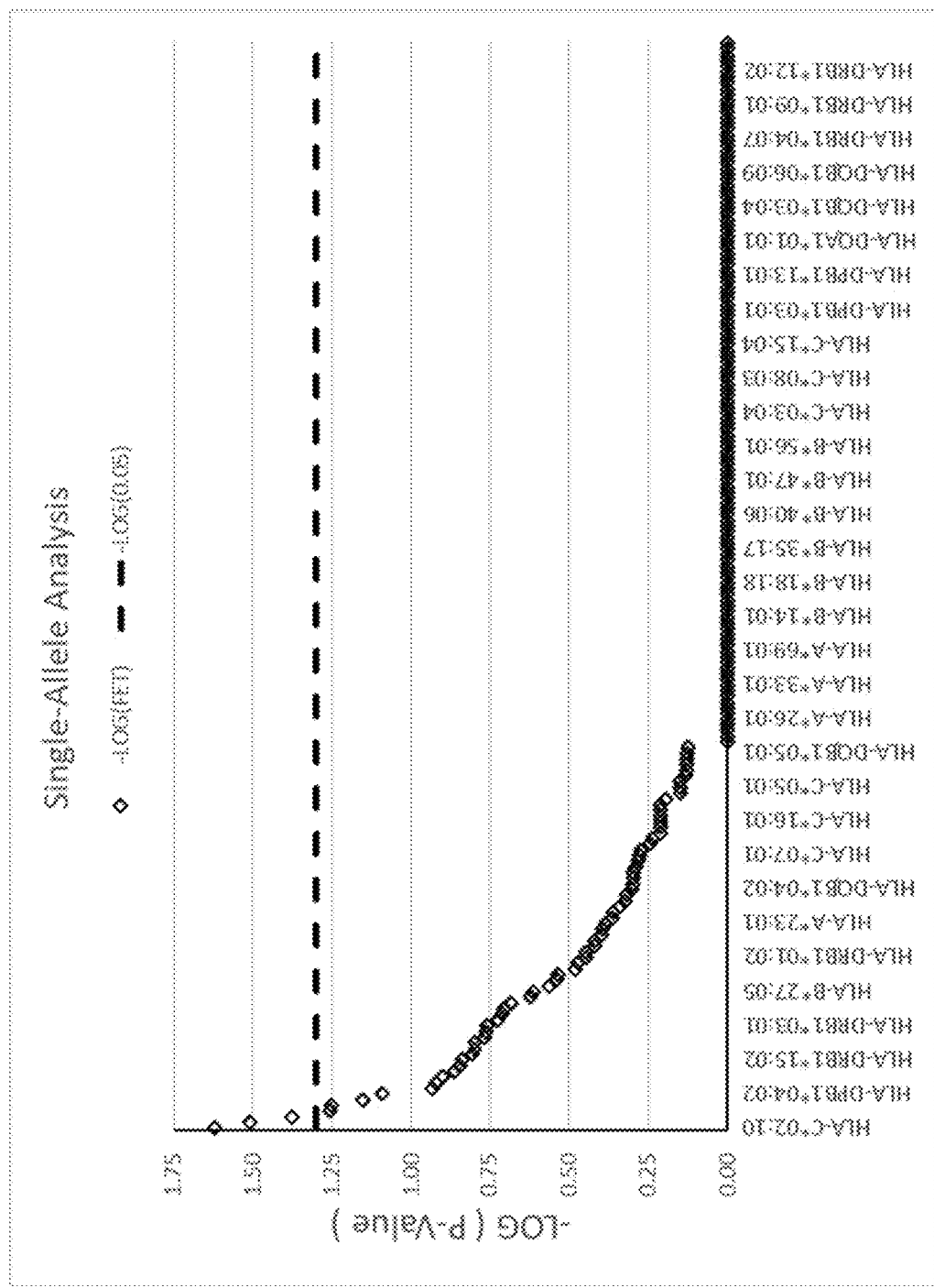
FIG. 1 shows the results of the single-allele analysis. P-value for each allele detected (x-axis) is shown in log scale (y-axis).

The present disclosure is related to the inventors' discovery that DILI in subjects treated with infliximab is associated with particular genetic variants. The present inventors discovered that a set of HLA alleles are present at significantly higher frequency in subjects that exhibited DILI after administration of infliximab. Accordingly, the present disclosure provides improved methods for treatment of diseases (e.g., autoimmune diseases) with infliximab in a defined patient population, and/or for reduction in the risk of DILI in the defined patient population.

Definitions

As used herein, the term "about" refers to an amount somewhat more or less than the stated parameter value, for example plus or minus five or ten percent of the object that "about" modifies, or as one of skill in the art would recognize from the context (e.g., approximately 50% of the interval between values). The term "about" also includes the value referenced. For example, a dose of about 1 mg includes 1 mg, as well as values somewhat below or above 1, such as 0.9 mg and 1.1 mg. As used herein, "and/or" refers to and encompasses any and all possible combinations of one or more of the associated listed items, as well as the lack of combinations when interpreted in the alternative ("or").

As used herein, the term "patient" refers to a human. In some embodiments, the patient can be a male or a female. In some embodiments, the patient can be an adult, or a pediatric patient. The term "subject" is used interchangeably herein with "patient." In some embodiments, the subject is a human that has a disease or condition that may be treated with infliximab. In some embodiments, prior to being treated with or prescribed infliximab for treatment of the disease or condition, the subject undergoes HLA testing. In other embodiments, a subject that has already been prescribed or begun treatment with infliximab undergoes HLA testing.

As used herein, a "patient population" is a group of patients who may be grouped together by a defining characteristic. For example, in some embodiments, the patient population provided herein is a population of patients having an HLA profile provided herein. In further embodiments, the patient population provided herein has an HLA profile provided herein, and is suffering from, at risk for, undergoing treatment for, or being evaluated for treatment for, an autoimmune or inflammatory disease. In some embodiments, the patient population provided herein has an HLA profile provided herein, and has been treated with, has been prescribed, has been considered for treatment with, may be treated with, or is being evaluated for treatment with, infliximab. In some embodiments, the patient population provided herein has an HLA profile provided herein, and is suffering from a disease or disorder for which infliximab may be administered as a therapeutic agent. In other embodiments, the patient population provided herein is a population from which patients having a particular HLA profile have been excluded. In certain embodiments, the patient population may have other defining characteristics relating to health status, age, sex, race, and/or ethnicity.

As used herein, a "patient treated with infliximab" or a "patient selected for infliximab therapy" or a "patient previously on infliximab" and the like refers to a patient having an indication which was amenable to treatment with infliximab.

As used herein, a "therapeutically effective regimen" refers to a treatment regimen of a duration and dosage sufficient to treat a disease or condition for which a drug is prescribed.

As used herein, a "dose" refers to the dosage of a drug, such as infliximab, for example, as indicated on the manufacture's FDA-approved label for the relevant indication or indications. As used herein, the term "dosing regimen" refers to the overall therapeutic regimen of a drug, such as infliximab. For example, a patient may be prescribed or administered a reduced dose of infliximab, and/or a reduced dose over time in a reduced dosing regimen. In some embodiments, the patient would not be administered, or would, in the physician's prescribed dosing regimen, be advised not to take infliximab. In some embodiments, the patient may have previously been prescribed or administered infliximab, and the administration of infliximab may be ceased temporarily or permanently in accordance with the methods provided herein.

Drug-Induced Liver Injury (DILI)

The term "adverse drug reaction" or "ADR," as used herein, refers to an undesired, unintended effect of a drug. ADRs can lead to severe disability or death in a subject.

Drug-induced liver injury (DILI) is one of the most common and serious ADRs, and can lead to product withdrawal post-approval. When severe, DILI causes acute liver failure, death, or a need to receive a liver transplantation for survival. In subjects with DILI, the injured cells include hepatocytes, bile duct epithelial cells, and vascular endothelial cells of the hepatic sinusoids and intrahepatic venous system. DILI can be acute or chronic, with patients suffering from acute DILI often exhibiting chronic DILI over time. The clinical manifestations of acute DILI may initially include varying elevations in the level of hepatic biochemical indexes including serum aspartate aminotransferase (AST; also called serum glutamic oxaloacetic transaminase, or SGOT), alanine aminotransferase (ALT; also called serum glutamate pyruvate transaminase or SGPT), alkaline phosphatase (ALP), and gamma-glutamyl transferase (GGT). Some patients with acute DILI may have symptoms such as fatigue, decreased appetite, aversion to oily food, tender liver, and epigastric discomfort. Patients may also exhibit jaundice, light-colored feces, and pruritus. Some acute DILI patients may have allergic manifestations including fever, rashes, increased eosinophils, and even aching pain in joints, which may be accompanied by other manifestations of extrahepatic organ damage. Some patients may develop into acute or subacute liver failure. Chronic DILI may present as, for example and without limitation, chronic hepatitis, liver fibrosis, compensated and decompensated cirrhosis, autoimmune hepatitis (AIH)-like DILI, chronic intrahepatic cholestasis, vanishing bile duct syndrome (VBDS), or a combination thereof. Patients may also present with sinusoidal obstruction syndrome (SOS)/hepatic veno-occlusive disease (VOD) or liver tumors. SOS/VOD may appear acutely with ascites, jaundice, and hepatomegaly.

DILI may be detected by monitoring levels of biochemical markers of liver function, such as AST, ALT, ALP, GGT, and bilirubin (TBil). Levels of any combination of these that are ULN (upper limit of normal) may indicate DILI. For example, DILI may be identified biochemically as reaching any of the following: (1) ALT≥5 ULN; (2) ALP≥2 ULN, especially in patients with elevated 5'-nucleotidase or GGT, and without bone-diseases-related ALP elevation; (3) ALT≥3 ULN and TBil≥2 ULN (see, e.g., Aithal G P, Watkins P B, Andrade R J. "Case definition and phenotype standardization in drug-induced liver injury." *Clin Pharmacol Ther.* 2011; 89(6):806-815). In some patients, a liver biopsy may be needed to determine the presence or extent of liver damage.

However, the monitoring of biochemical markers is often ineffective for reducing the risk of DILI in subjects receiving a therapeutic agent. When the drug cannot be predicted to cause liver injury in a particular patient population, DILI often goes undetected until severe damage occurs and/or progresses too fast to prevent severe damage. Thus, there is a serious need for a clinically useful method for predicting and preventing the development of DILI upon administration of a drug.

HLA Typing

As described herein, the present Applicants have found that certain classes of patients, i.e., patients having one or more of the particular HLA alleles or sets of HLA alleles provided herein, are at increased risk of developing DILI upon administration of infliximab.

The human leukocyte antigen (HLA) system describes the genetic locus encoding, among other immune-related genes, the major histocompatibility complex (MHC) proteins in humans. MHCs which are the proteins responsible for regulation of the immune system. HLA-A, HLA-B, and HLA-C are the three major antigen loci of MHC class I, which is the MHC class that presents peptides present inside the cell to CD8+ T cells. HLA-DP, HLA-DR, HLA-DQ, HLA-DM, and HLA-DO are the major loci of MHC class II, which present antigens from outside the cell to CD4+ T cells. Within these loci are pairs of alpha and beta chains: HLA-DPA1, HLA-DPB1, HLA-DRA, HLA-DRB1, HLA-DRB3, HLA-DRB4, HLA-DRB5, HLA-DQA1, HLA-DQA2, HLA-DQB1, HLA-DQB2, HLA-DMA, HLA-DMB, HLA-DOA, and HLA-DOB. The term "allele" refers herein to an alternative form of the gene at a given locus; alleles occupy the same locus on homologous chromosomes. Thus, an HLA allele is the specific allele present at a given HLA locus for an individual patient. The term "genetic variation" may be used herein to describe an HLA allele.

As used herein, "HLA typing" and the like refers to determining a subject's HLA profile, which is made up of the individual's HLA alleles. The HLA typing disclosed herein includes determining whether a particular HLA allele or set of alleles is present or absent in the patient. Various methods for HLA typing are known in the art, and any method for determining the presence or absence of HLA alleles can be used in the methods disclosed herein. HLA typing can be performed at low, intermediate, or high resolution. Low resolution HLA typing refers to typing wherein the alleles are reported at the two-digit level. An example of a representation of an HLA allele at the two-digit level is HLA-DQA1*01. Low resolution HLA typing can be achieved using serological methods. The standard method for serological HLA typing is the micro-lymphocytotoxicity assay, in which the lymphocytes of a subject are tested against a panel of antisera or monoclonal antibodies whose specificity for HLA has been previously characterized. Antibodies that bind to the HLA molecules induce lysis in the presence of complement, and indicate which HLA molecules were present on the subject's lymphocytes.

DNA- or RNA-based typing directly determines the sequence, and can provide intermediate or high resolution results. High resolution methods are preferred, in some embodiments, because tight linkage disequilibrium between genes and the high degree of polymorphism present at the MHC loci can make it difficult to obtain useful information with lower resolution methods. High resolution HLA typing may be achieved using DNA- or RNA-based methods and can provide HLA reporting at the four-digit level. An example of a representation of an HLA allele at the four-digit level is HLA-DQA1*01:03. Such methods include, without limitation, PCR-sequence-specific primer (SSP) typing, PCR-sequence specific oligonucleotide (SSO) hybridization, direct sequencing, sequence based typing (SBT; e.g., Sanger sequence based method of sequencing), next generation sequencing (NGS), and the like. PCR-SSP involves allele sequence-specific primer pairs that are designed to selectively amplify target sequences that are specific to a single allele, with PCR performed in the presence of control primer pairs matching non-allelic sequences present in the sample. PCR-SSO typing uses PCR target amplification, hybridization of PCR products to a panel of immobilized sequence-specific oligonucleotides on beads, and detection of probe-bound amplification product. SBT is based on PCR target amplification, followed by sequencing of the PCR products and data analysis. NGS is an approach that can be achieved using various methods, for example those discussed in Carapito et al., *Human Immunol.* 77(2016) 1016-23. In principle, NGS is similar to Sanger-based sequencing, in that the bases of a DNA fragment are identified sequentially from signals emitted as each fragment is resynthesized from a DNA template strand. NGS achieves this in a scaled-up manner by allowing millions of reactions to occur in parallel. Advantages of NGS include the ability to multiplex, that is, amplify and sequence multiple HLA genes in a single reaction. Those skilled in the art will appreciate that various commercially available kits and analysis software can be used to HLA type a sample.

Intermediate resolution HLA typing refers to a situation where four-digit level typing has been completed, but there are several possibilities for the HLA present. For example, in PCR-SSP, the PCR primers used may yield more than one possible genotype that an individual may have, which may require additional testing with additional combinations of primers and/or cloning and sequencing of the clones in order to obtain an unambiguous HLA type.

In some embodiments, methods for HLA typing and/or detection of HLA alleles are referred to as "genetic assays." Genetic assays can be used to detect the presence or absence of one or more genetic variations (e.g., one or more alleles).

For example, in some embodiments, the present disclosure provides methods for treating a subject in need of infliximab therapy or in need of treatment for an autoimmune disease or disorder, comprising testing the subject for the presence or absence of one or more genetic variations, using a genetic assay. In some embodiments, the one or more genetic variations are selected from the group consisting of HLA-B*39:01, HLA-C*12:03, HLA-DQA1*03:01, HLA-DPB1*04:02, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01. In particular embodiments, the genetic variation comprises the HLA-B*39:01 allele.

In one aspect, the present inventors found that a particular HLA allele was associated with the development of DILI after subjects were administered infliximab. The inventors undertook an extensive statistical analysis of the HLA alleles present in samples from subjects who experienced DILI following administration with infliximab, as compared to samples from healthy subjects (i.e., subjects who received infliximab and did not experience DILI) and found a statistically significant increased risk of developing DILI associated with HLA-B*39:01.

In another aspect, the present inventors found that a particular set of HLA alleles are associated with the development of DILI after subjects were administered infliximab. More specifically, the inventors undertook an extensive statistical analysis of the HLA alleles present in samples from subjects who experienced DILI following administration with infliximab, as compared to samples from healthy subjects (i.e., subjects who received infliximab and did not experience DILI). Each of the HLA profiles identified as being at a statistically significantly increased risk of developing DILI included at least one of the following HLA alleles: HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01.

In addition, the inventors assessed whether any two-allele, three-allele, four-allele, or greater than four-allele combinations exhibited a statistically significant increase in the risk of DILI following infliximab administration. The two-allele combinations, where the presence of at least one of the following sets of two alleles in an individual's HLA profile conferred statistically significant increase in the risk of DILI, were:

HLA-B*07:02, HLA-DQA1*01:03,
HLA-C*07:02, HLA-DQA1*01:03,
HLA-A*24:02, HLA-DQA1*01:03,
HLA-DQA1*03:03, HLA-DRB1*13:01,
HLA-DQA1*03:03, HLA-DQB1*06:03,
HLA-DQA1*01:03, HLA-DQA1*03:03,
HLA-DPB1*01:01, HLA-DQB1*02:01,
HLA-DPB1*01:01, HLA-DQA1*05:01, and
HLA-DPB1*01:01, HLA-DRB1*03:01.

The three-allele combinations, where the presence of at least one of the following sets of three alleles in an individual's HLA profile conferred statistically significant increase in the risk of DILI, were:

HLA-A*24:02, HLA-DQA1*01:03, HLA-DQA1*03:03,
HLA-A*24:02, HLA-DQA1*03:03, HLA-DQB1*06:03,
HLA-A*24:02, HLA-DQA1*03:03, HLA-DRB1*13:01,
HLA-A*24:02, HLA-B*07:02, HLA-DQA1*01:03,
HLA-B*07:02, HLA-DPB1*04:01, HLA-DQA1*01:03,
HLA-A*24:02, HLA-DPB1*04:01, HLA-DQA1*01:03,
HLA-C*07:02, HLA-DPB1*04:01, HLA-DQA1*01:03,
HLA-A*24:02, HLA-DQB1*03:01, HLA-DQB1*06:03,
HLA-A*24:02, HLA-DQB1*03:01, HLA-DRB1*13:01,
HLA-A*24:02, HLA-C*07:02, HLA-DQA1*01:03,
HLA-A*24:02, HLA-DQA1*01:03, HLA-DQB1*03:01,
HLA-B*07:02, HLA-C*07:02, HLA-DQA1*01:03,
HLA-DPB1*04:01, HLA-DQA1*01:03, HLA-DQA1*03:03,
HLA-DPB1*04:01, HLA-DQA1*03:03, HLA-DRB1*13:01,
HLA-DPB1*04:01, HLA-DQA1*03:03, HLA-DQB1*06:03,
HLA-A*02:01, HLA-C*03:03, HLA-DQA1*05:01,
HLA-A*02:01, HLA-C*03:03, HLA-DQB1*02:01,
HLA-A*02:01, HLA-C*03:03, HLA-DRB1*03:01,
HLA-A*02:01, HLA-A*24:02, HLA-DQA1*01:03,
HLA-DQA1*03:03, HLA-DQB1*03:01, HLA-DRB1*13:01,
HLA-A*02:01, HLA-DPB1*01:01, HLA-DQB1*02:01,
HLA-DQA1*01:03, HLA-DQA1*03:03, HLA-DQB1*03:01,
HLA-DQA1*03:03, HLA-DQB1*03:01, HLA-DQB1*06:03,
HLA-A*02:01, HLA-DPB1*01:01, HLA-DQA1*05:01, and
HLA-A*02:01, HLA-DPB1*01:01, HLA-DRB1*03:01.

The four-allele combinations, where the presence of at least one of the following sets of four alleles in an individual's HLA profile conferred statistically significant increase in the risk of DILI, were:
HLA-A*24:02, HLA-DPB1*04:01, HLA-DQA1*01:03, HLA-DQA1*03:03,
HLA-A*24:02, HLA-DPB1*04:01, HLA-DQA1*03:03, HLA-DQB1*06:03,\
HLA-A*24:02, HLA-DPB1*04:01, HLA-DQA1*03:03, HLA-DRB1*13:01,
HLA-A*24:02, HLA-DQA1*01:03, HLA-DQA1*03:03, HLA-DQB1*03:01,
HLA-A*24:02, HLA-DQA1*03:03, HLA-DQB1*03:01, HLA-DQB1*06:03,
HLA-A*24:02, HLA-DQA1*03:03, HLA-DQB1*03:01, HLA-DRB1*13:01,
HLA-A*24:02, HLA-DQA1*01:03, HLA-DQA1*03:03, HLA-DQB1*06:03,
HLA-A*24:02, HLA-DQA1*01:03, HLA-DQA1*03:03, HLA-DRB1*13:01,
HLA-A*24:02, HLA-DQA1*03:03, HLA-DQB1*06:03, HLA-DRB1*13:01, and
HLA-A*24:02, HLA-B*07:02, HLA-DPB1*04:01, HLA-DQA1*01:03.

In addition, certain higher level associations were determined to exhibit a statistically significant increase in the risk of DILI following infliximab administration. For example, the combination of the following alleles significantly increased the risk of DILI: HLA-C*07:01, HLA-DQA1*05:01, HLA-DQB1*02:01, HLA-DRB1*03:01, HLA-B*08:01, and HLA-DPB1*01:01; HLA-DPB1*04:01, HLA-DQA1*01:03, HLA-DQB1*03:01, HLA-DQA1*03:03, HLA-DQB1*06:03, HLA-DRB1*13:01, and HLA-DRB1*04:01; or HLA-DPB1*04:01, HLA-C*07:01, HLA-DQA1*05:01, HLA-DQB1*02:01, HLA-DRB1*03:01, HLA-A*01:01, HLA-B*08:01, and HLA-DPB1*01:01.

Infliximab

Infliximab is a mouse-human chimeric monoclonal antibody that binds to human tumor necrosis factor (TNF). Due to the importance of TNF in inflammatory processes, this inhibitory antibody has a potent anti-inflammatory effect. Infliximab has been approved for use in the United States for rheumatoid arthritis, ankylosing spondylitis, psoriatic arthritis, plaque psoriasis, Crohn's disease (adult and pediatric) and ulcerative colitis (adult and pediatric). Infliximab can be indicated for the treatment of moderate to severe active rheumatoid arthritis in patients who have had inadequate response or tolerance to methotrexate. Infliximab is also under clinical investigation for use in various other diseases and disorders, including, but not limited to, sterile corneal melt, depression, bipolar depression (e.g., bipolar I/II depression), refractory intestinal Behcet's disease, Takayasu's arteritis, dolichoectatic vertibrobasilar (DVB) aneurysms, refractory idiopathic scleritis, graft versus host disease (GVHD), steroid refractory acute graft versus host disease, macular edema, diabetic macular edema, refractory polymyalgia rheumatic (PMR), chroroidal neovascularization, Kawasaki disease, melanoma, advanced melanoma, inflammatory skin disease, sarcoidosis, and anal fistulae.

Infliximab is marketed under the trade name REMICADE®, and the FDA and European Medicines Agency (EMA) have also approved an infliximab biosimilar, INFLECTRA®. Various other biosimilars are also approved in some countries outside the US and/or are in development worldwide.

The dosing for infliximab varies by indication, but generally is administered intravenously at a dose of 5 mg/kg, and over several doses (e.g., at 1, 2, and 6 weeks, with a maintenance dose at 6 or 8 week intervals thereafter). In some embodiments, a therapeutically effective amount of infliximab is at least 5 mg/kg infliximab. For some patients, the prescribed dose may be increased to 10 mg/kg. For some patients with rheumatoid arthritis, infliximab may be administered in conjunction with methotrexate, and the prescribed dose of infliximab may be 3 mg/kg, with or without an increase to 10 mg/kg and/or a maintenance dose every 4, 6, or 8 weeks. Infliximab has been known to cause hepatotoxicity, and even severe hepatic reactions that can be fatal or necessitate a liver transplant. Generally, when a patient receiving infliximab exhibits jaundice and/or liver enzyme elevations, administration of infliximab is ceased. For some patients, corticosteroid treatment is needed once liver injury has presented. Subjects experiencing liver toxicity may be switched to an alternative therapeutic agent, such as etanercept, or other alternatives to infliximab.

In certain aspects of the present disclosure, there are provided methods for treating an autoimmune disease or other disease or disorder that may be amenable to treatment with infliximab; or methods for reducing the risk or severity of DILI in subjects having an autoimmune disease or other disease or disorder that may be amenable to treatment with infliximab. The methods include reducing the dose of infliximab; prescribing a dose of infliximab that is lower than the dose on the approved label or the previously prescribed or otherwise prescribed dose; ceasing administration of infliximab; and/or not administering infliximab to the subject, which includes administering an alternative to infliximab. For example, in some embodiments, the methods provided herein comprise administering infliximab to the subject in an amount of less than about 5 mg/kg, less than about 4.5 mg/kg, less than about 4 mg/kg, less than about 3.5 mg/kg, less than about 3 mg/kg, less than about 2.5 mg/kg, less than about 2 mg/kg, less than about 1.5 mg/kg, less than about 1 mg/kg, less than about 0.5 mg/kg, less than about 0.25 mg/kg, less than about 0.1 mg/kg, or less. In certain embodiments, the term "less than" a given dosing level encompasses a dose of 0 mg/kg. For example, in some embodiments, a subject who is administered "less than 5 mg/kg infliximab" is administered 0 mg/kg infliximab. Thus, in some embodiments, administration of "less than 5 mg/kg infliximab" and the like includes non-administration of infliximab. In some embodiments, the subjects who are administered a reduced dose of infliximab and/or are not administered infliximab in accordance with the methods provided herein are administered an alternative drug to treat the disease or disorder. Thus, in some embodiments, subjects are treated according to the methods provided herein with a therapeutic agent for the treatment of the autoimmune disease that is not infliximab. In some embodiments, the subject may be administered any drug known or suspected of treating the disease or disorder that the subject is suffering from. For example, in some embodiments, the subject is administered a cytokine inhibitor that is not infliximab. For example, the subject may be administered a TNF inhibitor that is not infliximab. In some embodiments, the subject is administered a drug or therapeutic agent that is not infliximab or is an alternative to infliximab, for example a drug or therapeutic agent selected from the group consisting of azathioprine, mercaptopurine, adalimumab, certolizumab, methotrexate, natalizumab, vedolizumab, ustekinumab, mesalamine, budesonide, hyoscyamine, celecoxib, hydroxychloroquin, etanercept, prednisone, cyclosporine, tocilizumab, meloxicam, leflunomide, sulfasalazine, abatacept, rituximab, golimumab, acitretin, secukinumab, apremilast, sarilumab, ixekizumab, corticotropin, olsalazine, balsalazide, tacrolimus, topiramate, cholestyramine, mycophenolate mofetil, dexamethasone, hydrocortisone, cromolyn, clonidine, diclofenac, naproxen, ibuprofen, aspirin, esomeprazole, tofacitinib, famotidine, nabumetone, etodolac, atorvastatin, anakinra, methylprednisone, triamcinolone, doxycycline, indomethacin, sulindac, tramadol, auranofin, misoprostol, ketoprofen, oxaprozin, piroxicam, salsalate, acetaminophen, hydrocodone, minocycline, alemtuzumab, flurbiprofen, cortisone, penicillamine, cyclophosphamide, diflunisal, fenoprofen, interferon gamma-1b, meclofenamate, phenytoin, tetracycline, tolmetin, hydroxyurea, betamethasone, calcipotriene, brodalumab, guselkumab, and tildrakizumab. In some embodiments, the therapeutic agent that is not infliximab or that is an alternative to infliximab includes any salts, esters, biosimilars, and the like of the additional or alternative therapeutic agents provided herein. Other drugs that may treat the disease or disorder from which the subject suffers will be apparent to one of ordinary skill in the art and are encompassed by the present disclosure.

Diseases and Disorders

In one aspect, the present disclosure provides methods for treating a subject having an autoimmune or inflammatory disease. Autoimmune or inflammatory diseases, in some embodiments, are selected from the group consisting of Crohn's disease, psoriasis (including plaque psoriasis), arthritis (including rheumatoid arthritis, psoriatic arthritis, osteoarthritis, or juvenile idiopathic arthritis), multiple sclerosis, ankylosing spondylitis, spondyloarthritis, inflammatory bowel diseases (IBD), ulcerative colitis, systemic lupus erythematosus, celiac disease, myasthenia gravis, type 1 narcolepsy, neuromyelitis optica, chorioretinopathy, pemphigus vulgaris, Behcet's disease, glomerulonephritis, type 1 diabetes mellitus, epidermolysis bullosa, Goodpasture Syndrome, uveitis, sepsis, neurodegenerative diseases, neuronal regeneration, spinal cord injury, primary and metastatic cancers, a respiratory disorder, asthma, allergic and nonallergic asthma, chronic obstructive pulmonary disease (COPD), a condition involving airway inflammation, eosinophilia, fibrosis and excess mucus production, cystic fibrosis, pulmonary fibrosis, an atopic disorder, atopic dermatitis, urticaria, eczema, allergic rhinitis, allergic enterogastritis, liver cirrhosis, liver fibrosis, and scleroderma.

In certain embodiments, the patient has an autoimmune disease. In some embodiments, the patient has a disease or condition selected from Crohn's disease, pediatric Crohn's disease, ulcerative colitis, pediatric ulcerative colitis, rheumatoid arthritis, ankylosing spondylitis, psoriatic arthritis, and plaque psoriasis.

In some embodiments, the patient has a disease or condition selected from the group consisting of sterile corneal melt, depression, bipolar depression (e.g., bipolar I/II depression), major depressive disorder (MDD), refractory intestinal Behcet's disease, Takayasu's arteritis, dolichoectatic vertibrobasilar (DVB) aneurysms, refractory idiopathic scleritis, graft versus host disease, steroid refractory acute graft versus host disease, macular edema, diabetic macular edema, refractory polymyalgia rheumatic (PMR), chroroidal neovascularization, Kawasaki disease, melanoma, advanced melanoma, inflammatory skin disease, sarcoidosis, and anal fistulae. In some embodiments, the patient is a recipient of an organ transplant such as a kidney transplant.

Methods

The present inventors surprisingly found that the risk of DILI upon administration of infliximab is significantly higher in subjects having a particular HLA allele or set of alleles. Thus, infliximab is contraindicated in the patient populations provided herein. This information can be used in methods for drastically improving the treatment of patients having diseases or disorders that may be indicated for treatment with infliximab. Patients can be HLA typed prior to or following initiation of an infliximab dosing regimen, and based on this information infliximab can be excluded from the patient's treatment regimen, or the patient can be administered a reduced dose or reduced dosing regimen of infliximab, or the administration of infliximab can be halted, based on the HLA typing and using the methods provided herein. Thus, in certain embodiments, the present disclosure provides new and improved methods for treating autoimmune diseases or other diseases that may be treated with infliximab; new and improved methods for reducing the risk of DILI, and other related improved methods. In particular embodiments, the methods relate to a defined patient population having an HLA profile provided herein.

In some embodiments, the present disclosure provides methods for treating a disease or disorder that may be amenable to treatment with infliximab. In further embodiments, the disclosure provides methods for treating a disease or disorder that may be amenable to treatment with infliximab in a subject and/or patient population having certain HLA alleles and/or combinations of alleles provided herein. In some embodiments, the present disclosure provides methods for treating an autoimmune disease. In further embodiments, the disclosure provides methods for treating an autoimmune disease in a subject and/or patient population having certain HLA alleles and/or combinations of alleles provided herein. In some embodiments, the methods relating to treating a disease or disorder (e.g., an autoimmune disease) that may be amenable to treatment with infliximab comprise determining or obtaining the HLA profile of a subject and, if the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, then (i) not administering infliximab to the subject; (ii) administering less than about 5 mg/kg infliximab to the subject (e.g., administering less than about 4 mg/kg, less than about 3 mg/kg, less than about 2 mg/kg, less than about 1 mg/kg or 0 mg/kg infliximab), (iii) administering an alternative to infliximab to the subject; (iv) administering infliximab to the subject at a reduced dosing level and/or frequency relative to the level and/or frequency that infliximab would have otherwise been administered, and/or (v) closely monitoring the subject for signs or symptoms of DILI.

In some embodiments, the present disclosure provides methods for reducing the risk of DILI. In further embodiments, the risk of developing DILI after administration of infliximab is high in subjects having certain HLA alleles and/or combinations of alleles provided herein, and the methods provided herein reduce the risk that the subject will develop DILI by providing a means for identifying the risk in a given patient or a population of patients, and reducing the risk. In some embodiments, the methods for reducing the risk of DILI in a subject comprise determining or obtaining the HLA profile of the subject and, if the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, then reducing the risk of DILI by (i) not administering infliximab to the subject; (ii) administering less than about 5 mg/kg infliximab to the subject (e.g., administering less than about 4 mg/kg, less than about 3 mg/kg, less than about 2 mg/kg, less than about 1 mg/kg or 0 mg/kg infliximab), (iii) administering an alternative to infliximab to the subject; (iv) administering infliximab to the subject at a reduced dosing level and/or frequency relative to the level and/or frequency that infliximab would have otherwise been administered, and/or (v) closely monitoring the subject for signs or symptoms of DILI.

In some embodiments, the methods provided herein can be used to reduce the severity of DILI, and/or speed the time to recovery from DILI that has occurred in a subject following administration of infliximab. Thus, in some embodiments, the present disclosure provides methods for reducing the severity of and/or speeding recovery from DILI in a subject that has received infliximab, comprising determining or obtaining the HLA profile of the subject and, if the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, then reducing the risk of DILI by (i) ceasing administration of infliximab to the subject; (ii) reducing the dose of infliximab to less than about 5 mg/kg (e.g., administering less than about 4 mg/kg, less than about 3 mg/kg, less than about 2 mg/kg, less than about 1 mg/kg or 0 mg/kg infliximab), (iii) administering an alternative to infliximab to the subject, (iv) closely monitoring the subject for signs or symptoms of DILI, and/or (v) treating the subject with a steroid or other drug indicated for treatment of DILI.

Race and/or ethnicity may confer varied genetic susceptibility to DILI. Subjects having the HLA profiles provided herein may be grouped or clustered into certain races or ethnicities. In some embodiments, the patient treated by the methods of the present disclosure can be characterized by two or more of the characteristics described herein. In some embodiments, the patient may have an HLA profile provided herein (e.g., at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, and/or a two-, three-, four-, five-, six-, seven-, or eight-allele combination provided herein, along with an advanced age and/or an underlying disease or infection such as infection with hepatitis B virus (HBV) and/or hepatitis C virus (HCV) and/or human immunodeficiency virus (HIV). In some embodiments, the patient may be of advanced age, a high BMI, or a low BMI.

In certain embodiments, an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof confers a heightened risk of DILI upon administration of infliximab to a patient population. In some embodiments, infliximab is contraindicated in the patient population having the HLA profile.

In certain embodiments, an HLA profile comprising at least one set of two-allele combinations selected from HLA-B*07:02 and HLA-DQA1*01:03; HLA-C*07:02 and HLA-DQA1*01:03; HLA-A*24:02 and HLA-DQA1*01:03; HLA-DQA1*03:03 and HLA-DRB1*13:01; HLA-DQA1*03:03 and HLA-DQB1*06:03; HLA-DQA1*01:03 and HLA-DQA1*03:03; HLA-DPB1*01:01 and HLA-DQB1*02:01; HLA-DPB1*01:01 and HLA-DQA1*05:01; and HLA-DPB1*01:01 and HLA-DRB1*03:01 confers a heightened risk of DILI upon administration of infliximab to a patient population. In some embodiments, infliximab is contraindicated in the patient population having the HLA profile comprising any of the two-allele combinations.

In certain embodiments, an HLA profile comprising at least one set of three-allele combinations selected from HLA-A*24:02, HLA-DQA1*01:03, and HLA-DQA1*03:

03; HLA-A*24:02, HLA-DQA1*03:03, and HLA-DQB1*06:03; HLA-A*24:02, HLA-DQA1*03:03, and HLA-DRB1*13:01; HLA-A*24:02, HLA-B*07:02, HLA-DQA1*01:03; HLA-B*07:02, HLA-DPB1*04:01, and HLA-DQA1*01:03; HLA-A*24:02, HLA-DPB1*04:01, and HLA-DQA1*01:03; HLA-C*07:02, HLA-DPB1*04:01, and HLA-DQA1*01:03; HLA-A*24:02, HLA-DQB1*03:01, and HLA-DQB1*06:03; HLA-A*24:02, HLA-DQB1*03:01, and HLA-DRB1*13:01; HLA-A*24:02, HLA-C*07:02, and HLA-DQA1*01:03; HLA-A*24:02, HLA-DQA1*01:03, and HLA-DQB1*03:01; HLA-B*07:02, HLA-C*07:02, and HLA-DQA1*01:03; HLA-DPB1*04:01, HLA-DQA1*01:03, and HLA-DQA1*03:03; HLA-DPB1*04:01, HLA-DQA1*03:03, and HLA-DRB1*13:01; HLA-DPB1*04:01, HLA-DQA1*03:03, and HLA-DQB1*06:03; HLA-A*02:01, HLA-C*03:03, and HLA-DQA1*05:01; HLA-A*02:01, HLA-C*03:03, and HLA-DQB1*02:01; HLA-A*02:01, HLA-C*03:03, and HLA-DRB1*03:01; HLA-A*02:01, HLA-A*24:02, and HLA-DQA1*01:03; HLA-DQA1*03:03, HLA-DQB1*03:01, and HLA-DRB1*13:01; HLA-A*02:01, HLA-DPB1*01:01, and HLA-DQB1*02:01; HLA-DQA1*01:03, HLA-DQA1*03:03, and HLA-DQB1*03:01; HLA-DQA1*03:03, HLA-DQB1*03:01, and HLA-DQB1*06:03; HLA-A*02:01, HLA-DPB1*01:01, and HLA-DQA1*05:01; and HLA-A*02:01, HLA-DPB1*01:01, and HLA-DRB1*03:01 confers a heightened risk of DILI upon administration of infliximab to a patient population. In some embodiments, infliximab is contraindicated in the patient population having the HLA profile comprising any of the three-allele combinations.

In certain embodiments, an HLA profile comprising at least one set of three-allele combinations selected from HLA-A*24:02, HLA-DPB1*04:01, HLA-DQA1*01:03, and HLA-DQA1*03:03; HLA-A*24:02, HLA-DPB1*04:01, HLA-DQA1*03:03, and HLA-DQB1*06:03; HLA-A*24:02, HLA-DPB1*04:01, HLA-DQA1*03:03, and HLA-DRB1*13:01; HLA-A*24:02, HLA-DQA1*01:03, HLA-DQA1*03:03, and HLA-DQB1*03:01; HLA-A*24:02, HLA-DQA1*03:03, HLA-DQB1*03:01, and HLA-DQB1*06:03; HLA-A*24:02, HLA-DQA1*03:03, HLA-DQB1*03:01, and HLA-DRB1*13:01; HLA-A*24:02, HLA-DQA1*01:03, HLA-DQA1*03:03, and HLA-DQB1*06:03; HLA-A*24:02, HLA-DQA1*01:03, HLA-DQA1*03:03, and HLA-DRB1*13:01; HLA-A*24:02, HLA-DQA1*03:03, HLA-DQB1*06:03, and HLA-DRB1*13:01; and HLA-A*24:02, HLA-B*07:02, HLA-DPB1*04:01, and HLA-DQA1*01:03 confers a heightened risk of DILI upon administration of infliximab to a patient population. In some embodiments, infliximab is contraindicated in the patient population having the HLA profile comprising any of the four-allele combinations.

In some embodiments, an HLA profile comprising HLA-B*39:01 confers a heightened risk of DILI upon administration of infliximab to a patient or patient population.

In certain embodiments, an HLA profile comprising HLA-C*07:01, DQA1*05:01, DQB1*02:01, DRB1*03:01, B*08:01, and DPB1*01:01 confers a heightened risk of DILI upon administration of infliximab to a patient population. In certain embodiments, an HLA profile comprising HLA-DPB1*04:01, HLA-DQA1*01:03, HLA-DQB1*03:01, HLA-DQA1*03:03, HLA-DQB1*06:03, HLA-DRB1*13:01, and HLA-DRB1*04:01 confers a heightened risk of DILI upon administration of infliximab to a patient population. In certain embodiments, an HLA profile comprising HLA-DPB1*04:01, HLA-C*07:01, HLA-DQA1*05:01, HLA-DQB1*02:01, HLA-DRB1*03:01, HLA-A*01:01, HLA-B*08:01, and HLA-DPB1*01:01 confers a heightened risk of DILI upon administration of infliximab to a patient population.

In some embodiments, the present disclosure provides methods for treating an autoimmune disease comprising administering less than 5 mg/kg infliximab (e.g., 0 mg/kg infliximab) and alternatively or additionally administering to the subject an alternative or additional therapeutic agent for the autoimmune disease, in a subject having an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof. In some embodiments, the present disclosure provides methods for treating an autoimmune disease comprising administering less than 5 mg/kg infliximab (e.g., 0 mg/kg infliximab) and alternatively or additionally administering to the subject an alternative or additional therapeutic agent for the autoimmune disease, in a subject having any of the two- three- or four-allele combinations provided herein. In some embodiments, the alternative or additional therapeutic agent is selected from the group consisting of azathioprine, mercaptopurine, adalimumab, certolizumab, methotrexate, natalizumab, vedolizumab, ustekinumab, mesalamine, budesonide, hyoscyamine, celecoxib, hydroxychloroquin, etanercept, prednisone, cyclosporine, tocilizumab, meloxicam, leflunomide, sulfasalazine, abatacept, rituximab, golimumab, acitretin, secukinumab, apremilast, sarilumab, ixekizumab, and corticotropin. In particular embodiments, the therapeutic agent that is not infliximab is selected from the group consisting of adalimumab, certolizumab, natalizumab, ustekinumab, vedolizumab, azathioprine, cyclosporine, methotrexate, mercaptopurin, etanercept, and rituximab.

In some embodiments, the alternative to infliximab and/or the therapeutic agent that is not infliximab and/or additional therapeutic agent is etanercept. Etanercept (ENBREL® and its biosimilars) is approved by the FDA for treatment of rheumatoid arthritis, psoriatic arthritis, ankylosing spondylitis, polyarticular juvenile idiopathic arthritis, and plaque psoriasis. Etanercept may be administered at a dose of about 5 mg, about 10 mg, about 25 mg, about 50 mg, about 75 mg, or about 100 mg. Alternatively etanercept may be administered at a dose of about 0.5 mg/kg, about 0.8 mg/kg, about 1 mg/kg, about 5 mg/kg, or about 10 mg/kg. Etanercept may be administered parenterally, such as by subcutaneous injection. Patients receiving etanercept as an additional agent or alternative to infliximab may receive, for example, a 50 mg subcutaneous dose of etanercept, once weekly. In some embodiments, the present disclosure provides methods for treating an autoimmune disease in a subject having an HLA profile defined herein (e.g., comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01), wherein the method comprises administering etanercept to the subject. In some embodiments, the subject has rheumatoid arthritis, psoriatic arthritis, ankylosing spondylitis, plaque psoriasis, Crohn's disease (adult or pediatric), or ulcerative colitis (adult or pediatric). In some embodiments, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and the subject is selected for infliximab therapy, but infliximab therapy is stopped, reduced, or never initiated, wherein the subject is administered etanercept as an additional therapeutic agent or an alternative to infliximab.

In some embodiments, the alternative to infliximab and/or the therapeutic agent that is not infliximab and/or additional therapeutic agent is methotrexate. Methotrexate (TREX-ALL® and others) is approved by the FDA for treatment of rheumatoid arthritis, polyarticular juvenile idiopathic arthritis, and psoriasis. Methotrexate may be administered at a dose of about 5 mg, about 7.5 mg, about 10 mg, about 15 mg, about 20 mg, about 25 mg, about 30 mg, or about 50 mg. Methotrexate may be administered orally or parenterally, such as by intramuscular, subcutaneous, or intravenous injection. In some embodiments, the present disclosure provides methods for treating an autoimmune disease in a subject having an HLA profile defined herein (e.g., comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01), wherein the method comprises administering methotrexate to the subject. In some embodiments, the subject has rheumatoid arthritis, psoriatic arthritis, ankylosing spondylitis, plaque psoriasis, Crohn's disease (adult or pediatric), or ulcerative colitis (adult or pediatric). In some embodiments, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and the subject is selected for infliximab therapy, but infliximab therapy is stopped, reduced, or never initiated, wherein the subject is administered methotrexate as an additional therapeutic agent or an alternative to infliximab.

In some embodiments, the alternative to infliximab and/or the therapeutic agent that is not infliximab and/or additional therapeutic agent is adalimumab. Adalimumab (HUMIRA® and its biosimilars) is approved by the FDA for treatment of rheumatoid arthritis, juvenile idiopathic arthritis, psoriatic arthritis, ankylosing spondylitis, Crohn's disease, and plaque psoriasis. Adalimumab may be administered at a dose of about 20 mg, about 25 mg, about 30 mg, about 35 mg, about 40 mg, about 50 mg, about 80 mg, about 120 mg, about 160 mg, or about 200 mg. Adalimumab may be administered parenterally, such as by intramuscular, subcutaneous, or intravenous injection. In some embodiments, adalimumab may be administered by subcutaneous injection of about 40 mg every other week, or about 80 mg or about 160 mg as an initial dose followed by 40 mg maintenance doses. In some embodiments, the present disclosure provides methods for treating an autoimmune disease in a subject having an HLA profile defined herein (e.g., comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01), wherein the method comprises administering adalimumab to the subject. In some embodiments, the subject has rheumatoid arthritis, psoriatic arthritis, ankylosing spondylitis, plaque psoriasis, Crohn's disease (adult or pediatric), or ulcerative colitis (adult or pediatric). In some embodiments, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and the subject is selected for infliximab therapy, but infliximab therapy is stopped, reduced, or never initiated, wherein the subject is administered adalimumab as an additional therapeutic agent or an alternative to infliximab.

In some embodiments, the alternative to infliximab and/or the therapeutic agent that is not infliximab and/or additional therapeutic agent is abatacept. Abatacept (ORENCIA® and its biosimilars) is approved by the FDA for treatment of rheumatoid arthritis and juvenile idiopathic arthritis. Abatacept may be administered at a dose of about 10 mg/kg, or about 100 mg, about 250 mg, about 500 mg, about 750 mg, or about 1000 mg. Abatacept may be administered parenterally, such as by intramuscular, subcutaneous, or intravenous injection. In some embodiments, abatacept may be administered via an intravenous loading dose followed by intravenous or subcutaneous dosing thereafter. In some embodiments, abatacept is administered weekly. In some embodiments, the present disclosure provides methods for treating an autoimmune disease in a subject having an HLA profile defined herein (e.g., comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01), wherein the method comprises administering abatacept to the subject. In some embodiments, the subject has rheumatoid arthritis, psoriatic arthritis, ankylosing spondylitis, plaque psoriasis, Crohn's disease (adult or pediatric), or ulcerative colitis (adult or pediatric). In some embodiments, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and the subject is selected for infliximab therapy, but infliximab therapy is stopped, reduced, or never initiated, wherein the subject is administered abatacept as an additional therapeutic agent or an alternative to infliximab.

In some embodiments, the alternative to infliximab and/or the therapeutic agent that is not infliximab and/or additional therapeutic agent is rituximab. Rituximab (RITUXAN® and its biosimilars) is approved by the FDA for treatment of leukemia, lymphoma, and rheumatoid arthritis. Rituximab may be administered in a dose of about 250 mg/m2, about 275 mg/m2, or about 500 mg/m2; or a dose of about 500 mg, about 1000 mg, or about 1500 mg. Rituximab may be administered to rheumatoid arthritis patients in combination with methotrexate. Rituximab may be administered to rheumatoid arthritis patients in courses of two 1000 mg infusions, each course separated by 16, 18, 20, 22, 24, or more weeks. Rituximab may be administered parenterally, such as by intramuscular, subcutaneous, or intravenous injection. In some embodiments, the present disclosure provides methods for treating an autoimmune disease in a subject having an HLA profile defined herein (e.g., comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01), wherein the method comprises administering rituximab to the subject. In some embodiments, the subject has rheumatoid arthritis, psoriatic arthritis, ankylosing spondylitis, plaque psoriasis, Crohn's disease (adult or pediatric), or ulcerative colitis (adult or pediatric). In some embodiments, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and the subject is selected for infliximab therapy, but infliximab therapy is stopped, reduced, or never initiated, wherein the subject is administered rituximab as an additional therapeutic agent or an alternative to infliximab.

In some embodiments, the alternative to infliximab and/or the therapeutic agent that is not infliximab and/or additional therapeutic agent is certolizumab. Certolizumab (CIMZIA® and its biosimilars) is approved by the FDA for treatment of rheumatoid arthritis, psoriatic arthritis, ankylosing spondylitis, and Crohn's disease. Certolizumab may be administered in a dose of about 100 mg, about 200 mg, about 300 mg, about 400 mg, or about 500 mg. In some embodiments, certolizumab may be administered at a dose of 400 mg, administered in two subcutaneous injections of 200 mg. In some embodiments, an initial 400 mg dose is followed by doses of 200 mg or 400 mg weekly or every other week after the initial dose. Certolizumab may be administered parenterally, such as by intramuscular, subcutaneous, or intravenous injection. In some embodiments, the present disclosure provides methods for treating an autoimmune disease in a subject having an HLA profile defined herein (e.g., comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01), wherein the method comprises administering certolizumab to the subject. In some embodiments, the subject has rheumatoid arthritis, psoriatic arthritis, ankylosing spondylitis, plaque psoriasis, Crohn's disease (adult or pediatric), or ulcerative colitis (adult or pediatric). In some embodiments, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and the subject is selected for infliximab therapy, but infliximab therapy is stopped, reduced, or never initiated, wherein the subject is administered certolizumab as an additional therapeutic agent or an alternative to infliximab.

In some embodiments, the alternative to infliximab and/or the therapeutic agent that is not infliximab and/or additional therapeutic agent is golimumab. Golimumab (SIMPONI® and its biosimilars) is approved by the FDA for treatment of rheumatoid arthritis, psoriatic arthritis, and ankylosing spondylitis. Golimumab may be administered in a dose of about 10 mg, about 25 mg, about 50 mg, or about 100 mg. In some embodiments, golimumab may be administered at a dose of about 50 mg once per month by subcutaneous injection. Golimumab may be administered parenterally, such as by intramuscular, subcutaneous, or intravenous injection. In some embodiments, the present disclosure provides methods for treating an autoimmune disease in a subject having an HLA profile defined herein (e.g., comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01), wherein the method comprises administering golimumab to the subject. In some embodiments, the subject has rheumatoid arthritis, psoriatic arthritis, ankylosing spondylitis, plaque psoriasis, Crohn's disease (adult or pediatric), or ulcerative colitis (adult or pediatric). In some embodiments, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and the subject is selected for infliximab therapy, but infliximab therapy is stopped, reduced, or never initiated, wherein the subject is administered golimumab as an additional therapeutic agent or an alternative to infliximab.

In some embodiments, the alternative to infliximab and/or the therapeutic agent that is not infliximab and/or additional therapeutic agent is natalizumab. Natalizumab (TYSABRI® and its biosimilars) is approved by the FDA for treatment of Crohn's disease and multiple sclerosis. Natalizumab may be administered in a dose of about 300 mg. Natalizumab may be administered parenterally, such as by intramuscular, subcutaneous, or intravenous injection. In some embodiments, natalizumab may be administered to subjects by intravenous infusion of about 300 mg once per month. In some embodiments, the present disclosure provides methods for treating an autoimmune disease in a subject having an HLA profile defined herein (e.g., comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01), wherein the method comprises administering natalizumab to the subject. In some embodiments, the subject has rheumatoid arthritis, psoriatic arthritis, ankylosing spondylitis, plaque psoriasis, Crohn's disease (adult or pediatric), or ulcerative colitis (adult or pediatric). In some embodiments, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and the subject is selected for infliximab therapy, but infliximab therapy is stopped, reduced, or never initiated, wherein the subject is administered natalizumab as an additional therapeutic agent or an alternative to infliximab.

In some embodiments, the alternative to infliximab and/or the therapeutic agent that is not infliximab and/or additional therapeutic agent is ustekinumab. Ustekinumab (STELARA® and its biosimilars) is approved by the FDA for treatment of Crohn's disease, plaque psoriasis, and psoriatic arthritis. Ustekinumab. may be administered in a dose of about 45 mg, about 90 mg, about 260 mg, about 390 mg, or about 520 mg. Ustekinumab may be administered parenterally, such as by intramuscular, subcutaneous, or intravenous injection. In some embodiments, ustekinumab may be administered to subjects by subcutaneous administration every 4 weeks, every 8 weeks or every 12 weeks; or by intravenous infusion followed by subcutaneous doses. In some embodiments, the present disclosure provides methods for treating an autoimmune disease in a subject having an HLA profile defined herein (e.g., comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01), wherein the method comprises administering ustekinumab to the subject. In some embodiments, the subject has rheumatoid arthritis, psoriatic arthritis, ankylosing spondylitis, plaque psoriasis, Crohn's disease (adult or pediatric), or ulcerative colitis (adult or pediatric). In some embodiments, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and the subject is selected for infliximab therapy, but infliximab therapy is stopped, reduced, or never initiated, wherein the subject is administered ustekinumab as an additional therapeutic agent or an alternative to infliximab.

In some embodiments, the alternative to infliximab and/or the therapeutic agent that is not infliximab and/or additional therapeutic agent is vedolizumab. Vedolizumab (ENTYVIO® and its biosimilars) is approved by the FDA for treatment of Crohn's disease and ulcerative colitis. Vedolizumab may be administered in a dose of about 300 mg. Vedolizumab may be administered parenterally, such as by intramuscular, subcutaneous, or intravenous injection. In some embodiments, vedolizumab may be administered to subjects by intravenous infusion, for example at initial dosing and two and six weeks after the initial dosing, and/or every 8 weeks thereafter. In some embodiments, the present disclosure provides methods for treating an autoimmune disease in a subject having an HLA profile defined herein (e.g., comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01), wherein the method comprises administering vedolizumab to the subject. In some embodiments, the subject has rheumatoid arthritis, psoriatic arthritis, ankylosing spondylitis, plaque psoriasis, Crohn's disease (adult or pediatric), or ulcerative colitis (adult or pediatric). In some embodiments, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and the subject is selected for infliximab therapy, but infliximab therapy is stopped, reduced, or never initiated, wherein the subject is administered vedolizumab as an additional therapeutic agent or an alternative to infliximab.

In some embodiments, the alternative to infliximab and/or the therapeutic agent that is not infliximab and/or additional therapeutic agent is azathioprine. Azathioprine (IMURAN® and others) is used for treatment of rheumatoid arthritis and other autoimmune diseases. Azathioprine may be administered orally in a dose of about 0.5 mg/kg, about 1 mg/kg, about 1.5 mg/kg, about 2 mg/kg, or about 2.5 mg/kg. Azathioprine may be administered orally, such as an oral daily dose. In some embodiments, the present disclosure provides methods for treating an autoimmune disease in a subject having an HLA profile defined herein (e.g., comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01), wherein the method comprises administering azathioprine to the subject. In some embodiments, the subject has rheumatoid arthritis, psoriatic arthritis, ankylosing spondylitis, plaque psoriasis, Crohn's disease (adult or pediatric), or ulcerative colitis (adult or pediatric). In some embodiments, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and the subject is selected for infliximab therapy, but infliximab therapy is stopped, reduced, or never initiated, wherein the subject is administered azathioprine as an additional therapeutic agent or an alternative to infliximab.

In some embodiments, the alternative to infliximab and/or the therapeutic agent that is not infliximab and/or additional therapeutic agent is cyclosporine. Cyclosporine (NEORAL® and others) is approved by the FDA for treatment of rheumatoid arthritis and psoriasis. Cyclosporine may be administered at a dose of about 1 mg/kg, about 1.5 mg/kg, about 1.75 mg/g, about 2 mg/kg, about 3 mg/kg, about 3.5 mg/kg, or about 4 mg/kg. Cyclosporine may be administered orally or parenterally. For example, cyclosporine may be administered orally twice per day. In some embodiments, the present disclosure provides methods for treating an autoimmune disease in a subject having an HLA profile defined herein (e.g., comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01), wherein the method comprises administering cyclosporine to the subject. In some embodiments, the subject has rheumatoid arthritis, psoriatic arthritis, ankylosing spondylitis, plaque psoriasis, Crohn's disease (adult or pediatric), or ulcerative colitis (adult or pediatric). In some embodiments, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and the subject is selected for infliximab therapy, but infliximab therapy is stopped, reduced, or never initiated, wherein the subject is administered cyclosporine as an additional therapeutic agent or an alternative to infliximab.

In some embodiments, the alternative to infliximab and/or the therapeutic agent that is not infliximab and/or additional therapeutic agent is mercaptopurin. Mercaptopurin is used for the treatment of Crohn's disease and ulcerative colitis. Mercaptopurin may be administered at a dose of about 0.5 mg/kg, 1 mg/kg, about 1.5 mg/kg, about 1.75 mg/g, about 2 mg/kg, about 3 mg/kg, about 3.5 mg/kg, or about 4 mg/kg. Mercaptopurin may be administered orally or parenterally. For example, mercaptopurin may be administered orally twice per day. In some embodiments, the present disclosure provides methods for treating an autoimmune disease in a subject having an HLA profile defined herein (e.g., comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01), wherein the method comprises administering mercaptopurin to the subject. In some embodiments, the subject has rheumatoid arthritis, psoriatic arthritis, ankylosing spondylitis, plaque psoriasis, Crohn's disease (adult or pediatric), or ulcerative colitis (adult or pediatric). In some embodiments, the subject has an HLA profile comprising at least one HLA allele selected from the group consisting of HLA-B*39:01, HLA-C*12:03, HLA-DQA1*03:01, HLA-DPB1*04:02, HLA-DQA1*03:03, HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, HLA-C*03:03, HLA-C*07:01, HLA-A*01:01, HLA-B*08:01, and HLA-DRB1*04:01, or any combination thereof, and the subject is selected for infliximab therapy, but infliximab therapy is stopped, reduced, or never initiated, wherein the subject is administered mercaptopurin as an additional therapeutic agent or an alternative to infliximab.

All documents, including patents, applications, and non-patent publications cited herein are incorporated herein in their entireties for all purposes.

EXAMPLES

Example 1. HLA Analysis of Patients with ADR Following Exposure to Infliximab

A set of 12 samples from subjects that had been treated with infliximab and had experienced drug-induced liver injury (DILI) (hereinafter referred to as "diseased samples") were HLA tested and compared to a set of 10,397 healthy control samples (hereinafter referred to as "healthy samples"). The healthy samples were obtained from a general population of human subjects who did not experience DILI, and who may or may not have been exposed to infliximab. Analysis of a patient's genomic HLA profile and a robust statistical analysis was performed to identify HLA alleles and/or sets of alleles that are risk factors for the development of DILI following infliximab exposure.

In the first analysis of the infliximab samples, the inventors sought to find if the proportion of diseased samples exposed to an allele varied significantly from the proportion of the healthy samples with that allele. In order to do so, for each allele in the dataset (192 total), the inventors calculated the number of diseased samples present for an allele (a below), the number of diseased samples absent for the allele (c), the number of healthy samples present for the allele (b), and the number of healthy samples absent for the allele (d) (Table 1). Presence was defined as being either homozygous or heterozygous for an allele in question. A two-sided Fisher's Exact Test (FET) was performed on the data to calculate p-values.

TABLE 1

Set-up of analysis

|  | Diseased | Healthy |
|---|---|---|
| Allele Present | a | b |
| Allele Absent | c | d |

The results from the single allele analysis are provided in FIG. 1, which lists each allele's p-value on a logarithmic scale.

The results of the FET yielded three p-values below the standard 0.05 significance threshold. In order to account for the high number of hypotheses tested (192 total), the inventors then performed the Benjamini-Hochberg (BH) correction procedure for multiple comparisons. As this is an initial screening for potentially significant allele-drug interactions with a relatively small sample size, the false discovery rate (Q) was set to twenty percent, or 0.2.

Figure 2:
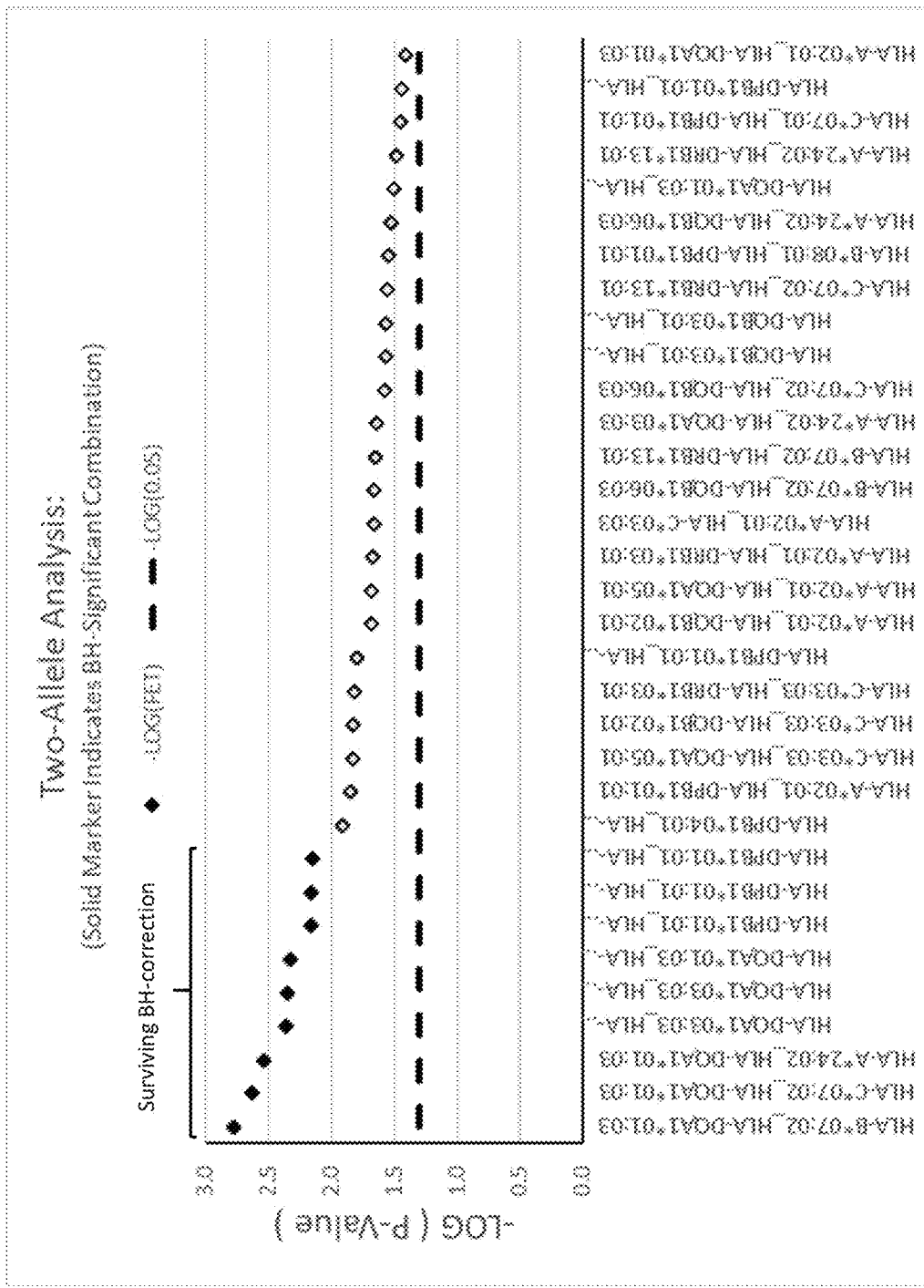
FIG. 2 shows the results of the two-allele analysis. P-value for each two-allele combination (x-axis) is shown in log scale (y-axis). The two-allele combinations with statistical significance surviving the BH correction are indicated in the figure and in Table 2.

In the second analysis of the infliximab samples, the inventors sought to find two-allele combinations that varied significantly in the diseased samples as compared to the healthy samples. In order to avoid testing unrealistic or extremely doubtful hypotheses, the inventors only tested for combinations in which each allele appeared at least three times individually (that is, they were present in at least 25% of the diseased samples). Likewise, only homozygous combinations that appeared at least three times were tested. These criteria dramatically reduced the number of hypotheses tested, from 36,864 to 211. Once again, the inventors invoked the BH procedure with Q equal to 0.2 in order to account for the amount of hypotheses tested, which reduced the number of significant results from 33 to 9. FIG. 2 is a plot of significant two-allele combinations, with those surviving BH-correction indicated.

Table 2. is the corresponding table showing the FET p-value, odds ratio (OR), and Benjamini Hochberg critical value, (i/m)Q, for the BH-significant two-allele combinations.

TABLE 2

Two-allele combinations

| Combination | P-value | OR | (i/m)Q |
|---|---|---|---|
| HLA-B*07:02, HLA-DQA1*01:03 | 1.69E−03 | 15.92 | 9.48E−04 |
| HLA-C*07:02, HLA-DQA1*01:03 | 2.37E−03 | 14.09 | 1.90E−03 |
| HLA-A*24:02, HLA-DQA1*01:03 | 2.90E−03 | 13.09 | 2.84E−03 |
| HLA-DQA1*03:03, HLA-DRB1*13:01 | 4.41E−03 | 23.93 | 3.79E−03 |
| HLA-DQA1*03:03, HLA-DQB1*06:03 | 4.51E−03 | 23.66 | 4.74E−03 |
| HLA-DQA1*01:03, HLA-DQA1*03:03 | 4.71E−03 | 23.12 | 5.69E−03 |
| HLA-DPB1*01:01, HLA-DQB1*02:01 | 6.86E−03 | 6.85 | 6.64E−03 |
| HLA-DPB1*01:01, HLA-DQA1*05:01 | 6.97E−03 | 6.82 | 7.58E−03 |
| HLA-DPB1*01:01, HLA-DRB1*03:01 | 7.04E−03 | 6.80 | 8.53E−03 |

Figure 3:
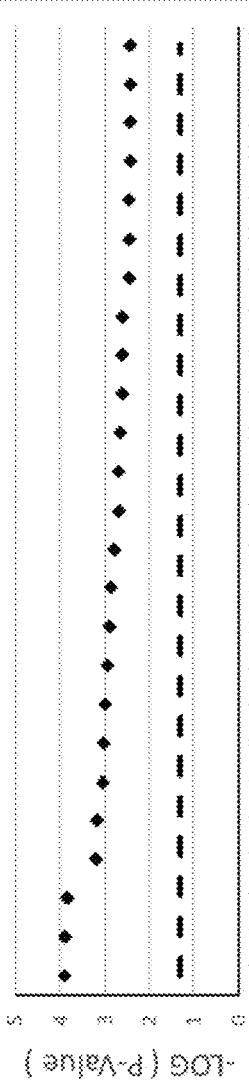
FIG. 3 shows the results of the three-allele analysis. The figure shows each three-allele combination having a statistical significance that survived the BH correction. P-value for each three-allele combination (x-axis) is shown in log scale (y-axis).

In the third analysis of the infliximab samples, the inventors sought to find three-allele combinations that varied significantly in the diseased samples as compared to the healthy samples. As with the two-allele combinations, the inventors only tested for combinations in which each allele appeared in at least 25% of our diseased samples. In addition to a frequency threshold, the inventors only sought combinations that were biologically possible. Thus any combinations with more than two alleles per locus were removed. These criteria dramatically reduced the number of hypotheses tested, from 1,216,480 to 1,336. Again the inventors invoked the BH procedure with Q equal to 0.2 in order to account for the amount of hypotheses tested, which reduced the number of significant results from 152 to 25. FIG. 3 is a plot of BH-significant three-allele combinations, and Table 3. provides the corresponding combination name, p-value, odds ratio, and Benjamini-Hochberg critical value

TABLE 3

Three-allele combinations

| Combination | P-value | OR | (i/m)Q |
|---|---|---|---|
| HLA-A*24:02, HLA-DQA1*01:03, HLA-DQA1*03:03 | 1.27E−04 | 157.88 | 1.50E−04 |
| HLA-A*24:02, HLA-DQA1*03:03, HLA-DQB1*06:03 | 1.27E−04 | 157.88 | 2.99E−04 |
| HLA-A*24:02, HLA-DQA1*03:03, HLA-DRB1*13:01 | 1.45E−04 | 146.62 | 4.49E−04 |
| HLA-A*24:02, HLA-B*07:02, HLA-DQA1*01:03 | 6.31E−04 | 66.55 | 5.99E−04 |
| HLA-B*07:02, HLA-DPB1*04:01, HLA-DQA1*01:03 | 6.70E−04 | 22.14 | 7.49E−04 |
| HLA-A*24:02, HLA-DPB1*04:01, HLA-DQA1*01:03 | 8.89E−04 | 20.03 | 8.98E−04 |
| HLA-C*07:02, HLA-DPB1*04:01, HLA-DQA1*01:03 | 9.34E−04 | 19.67 | 1.05E−03 |
| HLA-A*24:02, HLA-DQB1*03:01, HLA-DQB1*06:03 | 1.02E−03 | 51.56 | 1.20E−03 |
| HLA-A*24:02, HLA-DQB1*03:01, HLA-DRB1*13:01 | 1.12E−03 | 49.11 | 1.35E−03 |
| HLA-A*24:02, HLA-C*07:02, HLA-DQA1*01:03 | 1.28E−03 | 45.88 | 1.50E−03 |
| HLA-A*24:02, HLA-DQA1*01:03, HLA-DQB1*03:01 | 1.33E−03 | 44.87 | 1.65E−03 |

TABLE 3-continued

Three-allele combinations

| Combination | P-value | OR | (i/m)Q |
|---|---|---|---|
| HLA-B*07:02, HLA-C*07:02, HLA-DQA1*01:03 | 1.62E−03 | 16.15 | 1.80E−03 |
| HLA-DPB1*04:01, HLA-DQA1*01:03, HLA-DQA1*03:03 | 2.01E−03 | 36.20 | 1.95E−03 |
| HLA-DPB1*04:01, HLA-DQA1*03:03, HLA-DRB1*13:01 | 2.08E−03 | 35.56 | 2.10E−03 |
| HLA-DPB1*04:01, HLA-DQA1*03:03, HLA-DQB1*06:03 | 2.15E−03 | 34.95 | 2.25E−03 |
| HLA-A*02:01, HLA-C*03:03, HLA-DQA1*05:01 | 2.43E−03 | 32.73 | 2.40E−03 |
| HLA-A*02:01, HLA-C*03:03, HLA-DQB1*02:01 | 2.43E−03 | 32.73 | 2.54E−03 |
| HLA-A*02:01, HLA-C*03:03, HLA-DRB1*03:01 | 2.43E−03 | 32.73 | 2.69E−03 |
| HLA-A*02:01, HLA-A*24:02, HLA-DQA1*01:03 | 3.40E−03 | 27.45 | 2.84E−03 |
| HLA-DQA1*03:03, HLA-DQB1*03:01, HLA-DRB1*13:01 | 3.49E−03 | 27.09 | 2.99E−03 |
| HLA-A*02:01, HLA-DPB1*01:01, HLA-DQB1*02:01 | 3.54E−03 | 12.17 | 3.14E−03 |
| HLA-DQA1*01:03, HLA-DQA1*03:03, HLA-DQB1*03:01 | 3.57E−03 | 26.73 | 3.29E−03 |
| HLA-DQA1*03:03, HLA-DQB1*03:01, HLA-DQB1*06:03 | 3.57E−03 | 26.73 | 3.44E−03 |
| HLA-A*02:01, HLA-DPB1*01:01, HLA-DQA1*05:01 | 3.57E−03 | 12.12 | 3.59E−03 |
| HLA-A*02:01, HLA-DPB1*01:01, HLA-DRB1*03:01 | 3.61E−03 | 12.08 | 3.74E−03 |

Figure 4:
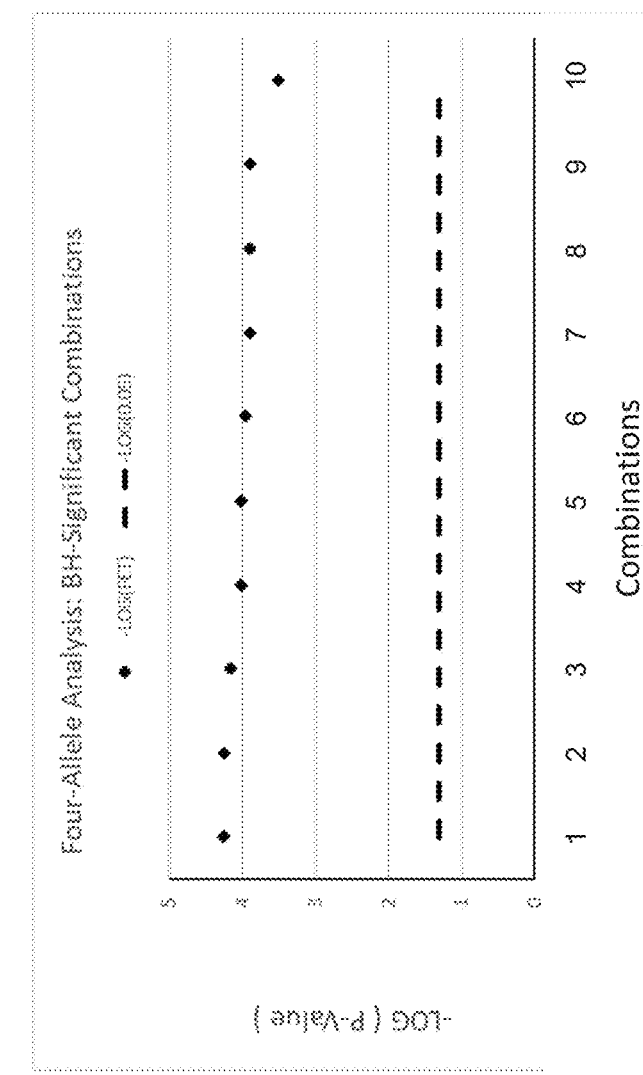
FIG. 4 shows the results of the four-allele analysis. The figure shows each four-allele combination having a statistical significance that survived the BH correction. P-value for each four-allele combination (x-axis) is shown in log scale (y-axis).

In the fourth analysis of the infliximab samples, the inventors sought to find four-allele combinations that varied significantly in the diseased samples as compared to the healthy samples. The criteria for this level of analysis were identical to the three-allele analysis. These criteria dramatically reduced the number of hypotheses tested, from 59,570,608 to 5,931. Again the inventors invoked the BH procedure with Q equal to 0.2 in order to account for the amount of hypotheses tested, which reduced the number of significant results from 399 to 10. FIG. 4 is a plot of BH-significant four-allele combinations, and Table 4. below is the corresponding table containing the allele combination, p-value, odds ratio, and Benjamini-Hochberg critical value.

TABLE 4

Four-allele combinations

| Combination | P-value | OR | (i/m)Q |
|---|---|---|---|
| HLA-A*24:02, HLA-DPB1*04:01, HLA-DQA1*01:03, HLA-DQA1*03:03 | 5.45E−05 | 256.06 | 3.37E−05 |
| HLA-A*24:02, HLA-DPB1*04:01, HLA-DQA1*03:03, HLA-DQB1*06:03 | 5.45E−05 | 256.06 | 6.74E−05 |
| HLA-A*24:02, HLA-DPB1*04:01, HLA-DQA1*03:03, HLA-DRB1*13:01 | 6.66E−05 | 227.32 | 1.01E−04 |
| HLA-A*24:02, HLA-DQA1*01:03, HLA-DQA1*03:03, HLA-DQB1*03:01 | 9.44E−05 | 186.50 | 1.35E−04 |
| HLA-A*24:02, HLA-DQA1*03:03, HLA-DQB1*03:01, HLA-DQB1*06:03 | 9.44E−05 | 186.50 | 1.69E−04 |
| HLA-A*24:02, HLA-DQA1*03:03, HLA-DQB1*03:01, HLA-DRB1*13:01 | 1.10E−04 | 171.48 | 2.02E−04 |
| HLA-A*24:02, HLA-DQA1*01:03, HLA-DQA1*03:03, HLA-DQB1*06:03 | 1.27E−04 | 157.88 | 2.36E−04 |
| HLA-A*24:02, HLA-DQA1*01:03, HLA-DQA1*03:03, HLA-DRB1*13:01 | 1.27E−04 | 157.88 | 2.70E−04 |
| HLA-A*24:02, HLA-DQA1*03:03, HLA-DQB1*06:03, HLA-DRB1*13:01 | 1.27E−04 | 157.88 | 3.03E−04 |
| HLA-A*24:02, HLA-B*07:02, HLA-DPB1*04:01, HLA-DQA1*01:03 | 3.04E−04 | 97.81 | 3.37E−04 |

A total of 14 different alleles were identified as present in at least one of the combination analyses. The alleles are: HLA-DQA1*01:03, HLA-B*07:02, HLA-C*07:02, HLA-A*24:02, HLA-DQA1*03:03, HLA-DRB1*13:01, HLA-DQB1*06:03, HLA-DPB1*01:01, HLA-DQB1*02:01, HLA-DQA1*05:01, HLA-DRB1*03:01, HLA-DPB1*04:01, HLA-DQB1*03:01, HLA-A*02:01, and HLA-C*03:03. In the two-, three-, and four-allele combinations analyses, each of these identified alleles appeared in at least three of the combination sets.

Following the four-allele analysis, we used inspection to search for potential higher-level associations. During this analysis we discovered three combinations that exhibited an increase in frequency in the diseased samples. The first combination included the following alleles: HLA-DPB1*04:01, HLA-C*07:01, HLA-DQA1*05:01, HLA-DQB1*02:01, HLA-DRB1*03:01, HLA-A*01:01, HLA-B*08:01, and HLA-DPB1*01:01. Out of the 12 diseased samples, two individuals (16.7%) had this eight-allele combination while 199 of the 10397 (1.91%) healthy samples had it. This resulted in a FET p-value of 2.16E-02 with an OR of 10.24 (95% CI 1.08-48.52). The next combination we investigated included the following alleles: HLA-DPB1*04:01, HLA-DQA1*01:03, HLA-DQB1*03:01, HLA-DQA1*03:03, HLA-DQB1*06:03, HLA-DRB1*13:01, and HLA-DRB1*04:01. Two diseased samples (16.7%) had this combination, and only 43 healthy samples (0.41%), which resulted in a p-value of 1.17E-03 and OR of 47.95 (95% CI 4.97-234.85). Lastly, we investigated the following six-allele combination, which is a subset of the eight-allele combination mentioned above: HLA-C*07:01, HLA-DQA1*05:01, HLA-DQB1*02:01, HLA-DRB1*03:01, HLA-B*08:01, and HLA-DPB1*01:01. Three diseased samples (25%) had this combination, as compared to 573 healthy samples (5.51%), which resulted in a FET p-value of 2.55E-02 and OR 5.71 (95% CI 0.99-22.97).

After accounting for overlap of individuals with the distinct allele combinations, we found that five diseased individuals (41.7%) had either of the last two combinations, while only 616 healthy samples (5.92%) had at least one of the combinations. This resulted in FET 4.14E-04 and OR 11.33 (95% CI 2.83-41.63).

Example 2. Further HLA Analysis of Patients with ADR Following Exposure to Infliximab A set of 25 additional samples from subjects that had been treated with infliximab and had experienced DILI were obtained. These are referred to as "cases" here. These samples were compared to a set of 60 matched controls. The matched controls were patients who received infliximab for at least one year and did not experience DILI. The controls were matched for age, sex, ethnicity, and BMI where possible. Statistical analyses were performed to identify from these cases HLA alleles that are risk factors for the development of DILI following infliximab exposure. Significant alleles were determined using Fischer's Exact Test (FET) (p<0.05).

As a secondary comparison, the HLA profiles of the 25 cases were compared to reference populations available at www.allelefrequencies.net. For calculating population presence rates, reference list entries were found by searching for "Caucasoid" ethnic origin subjects of gold-standard studies involving ≥100 subjects for alleles of interest on allelefrequencies.net. Sample sizes for the references represent the reported number of subjects directly typed for a given locus (i.e. USA NMDP European Caucasian reports 1,242,890 subjects typed for HLA-B and DRB1, but only 395,676 subjects typed for HLA-C; see Table 5).

In order to test for significant differences between the 25 Infliximab-DILI cases and the reference populations using Fisher's Exact Test (FET), counts of individuals carrying at least one copy of the allele in question were calculated one of two ways. If the population presence rate was available, the number of individuals was estimated by rounding the product of the population presence rate and the sample size for that HLA locus in that study. If no population presence rate was available, this number was estimated using the allele frequency rate and assuming Hardy-Weinberg equilibrium (HWE). That is, if the allele frequency is p, the number of individuals with the allele in question were calculated as $[p^2+2*p*(1-p)]*N_{samples}$, where $p^2+2*p*(1-p)$ represents the percentage of carriers if HWE is assumed, and $N_{samples}$ is the reference sample size for that locus.

TABLE 5

| Reference List | | | |
|---|---|---|---|
| Allele | Ref # | Sample Size | Population Reference Study |
| B*39:01 | Ref 1 | 1,242,890 | USA NMDP European Caucasian |
|  | Ref 2 | 298 | England Northwest |
| C*12:03 | Ref 1 | 395,676 | USA NMDP European Caucasian |
|  | Ref 2 | 604 | UK Pop 3 |
| DRB1*03:01 | Ref 1 | 1,242,890 | USA NMDP European Caucasian |
|  | Ref 2 | 141 | USA Philadelphia Caucasian |
| DQB1*02:01 | Ref 1 | 222 | USA San Antonio Caucasian |
|  | Ref 2 | 141 | USA Philadelphia Caucasian |
| DQA1*3:03 | Ref 1 | 171 | USA Caucasian Bethestda |
|  | Ref 2 | 155 | Netherlands pop 2 |

TABLE 5-continued

A summary of the alleles with significant results in the cases vs. controls individual data sets is provided in FIG. 5. The data sets individually analyzed were: Caucasian typed and/or Caucasian imputed; African typed and/or African imputed; and All Ethnicities typed and/or All Ethnicities imputed. "Typed only" means that only subjects with directly typed HLA alleles were considered in the indicated analysis. "Imputed only" means that only the imputed alleles (i.e., the subject's HLA profile was determined using known proxies for HLA subtypes in their genetic sequence) for each subject were used in the indicated analysis. "Imputed+ Typed" means that all subjects were considered; here, directly typed HLA alleles were used if available, otherwise, imputed alleles were used.

Table 6 provides a summary of the best reported FETs and associated Odds Ratio (OR) for the indicated alleles. Of particular note, HLA-B*39:01 was present in 4/25 cases and absent in 100% of controls, for an FET of 6.25E-03 and an OR of 25.33.

TABLE 6

| Summary of best reported FET | | | | | | | |
|---|---|---|---|---|---|---|---|
| Variant | Case Present | Case Absent | Control Present | Control Absent | FET | OR | Dataset |
| HLA-B*39:01 | 4 | 21 | 0 | 60 | 6.25E-03 | 25.33 | Caucasian imputed + typed |
| HLA-C*12:03 | 6 | 19 | 3 | 57 | 1.69E-02 | 5.85 | Caucasian imputed + typed |
| HLA-DQA1*03:01 | 4 | 27 | 23 | 43 | 2.93E-02 | 0.28 | All ethnicities imputed + typed |
| HLA-DPB1*04: 02 | 3 | 0 | 1 | 5 | 4.76E-02 | 25.67 | African imputed + typed |

Table 7A provides the overall presence rate and allele frequency of the indicated significant alleles in the cases and controls as compared to calculated and/or estimated population presence rates (Ref 1 and/or Ref 2). As above, significant alleles were determined using Fischer's Exact Test (FET) (p<0.05). The FET and associated Odds Ratio (OR) are reported in Table 5B. In some cases the population presence rate—the percentage of individuals in the population who are expected to carry at least one copy of the allele in question—is reported along with the allele frequency rate as a whole, otherwise it is given as "NR" for "not reported" (Table 5A).

TABLE 7A

Presence Rate and Allele Frequency

| | Counts | | Presence Rate (%) | | | | Allele Frequency | | | |
|---|---|---|---|---|---|---|---|---|---|---|
| Allele | Cases (25) | Controls (60) | Cases | Controls | Ref 1 | Ref 2 | Case | Control | Ref 1 | Ref 2 |
| B*39:01 | 4 | 0 | 16% | 0.0% | NR | 1.3% | 8% | 0.0% | 1.1% | 0.7% |
| C*12:03 | 6 | 3 | 24% | 5.0% | NR | 6.5% | 12% | 2.5% | 4.9% | 3.2% |
| DRB1*03:01 | 10 | 8 | 40% | 13.3% | NR | 15.6% | 20% | 6.7% | 12.2% | 7.8% |
| DQB1*02:01 | 10 | 7 | 40% | 11.7% | NR | 15.6% | 20% | 5.8% | 11.0% | 7.8% |
| DQA1*03:03 | 3 | 0 | 12% | 0.0% | 12.9% | 13.5% | 6% | 0.0% | 7.3% | 7.0% |

TABLE 7B

Fischer's Exact Test (FET) and Odds Ratio (OR)

| | FET vs. | | | OR vs. | | |
|---|---|---|---|---|---|---|
| Allele | Control | Ref 1 | Ref 2 | Control | Ref 1 | Ref 2 |
| B*39:01 | 0.01 | 0.00 | 0.00 | 25.33 | 8.33 | 13.72 |
| C*12:03 | 0.02 | 0.03 | 0.01 | 5.85 | 3.02 | 4.56 |
| DRB1*03:01 | 0.01 | 0.05 | 0.01 | 4.24 | 2.25 | 3.57 |
| DQB1*02:01 | 0.01 | 0.04 | 0.01 | 4.93 | 2.54 | 3.57 |
| DQA1*3:03 | 0.02 | 1.00 | 1.00 | 18.82 | 0.92 | 0.87 |

In summary, the studies showed that particular HLA alleles are associated with a higher risk of DILI following infliximab administration. In particular, HLA-B*39:01 was associated with a higher risk of DILI. The studies also showed that a set of defined HLA alleles (and/or particular two-, three-, four-, five-, six-, seven-allele, or more, combinations) are associated with higher risk of DILI following infliximab administration. The results of the study can be used to provide new means of reducing the risk of DILI in patient populations, and/or new methods for treating autoimmune disease in the patient populations.

The invention claimed is:

1. A method of treating a population of patients having an autoimmune disease with infliximab, the method comprising
providing a first population of patients having an autoimmune disease;
excluding only patients having an HLA profile comprising HLA-B*39:01 from the first population of patients;
treating the population of patients not excluded from the first population with infliximab; and
treating the excluded patients with an autoimmune disease therapy that is not infliximab.

2. The method of claim 1, wherein the HLA profile is or has been obtained using a polymerase chain reaction (PCR)-based approach, a direct sequencing approach, a next generation (NGS) approach and/or a direct HLA typing test.

3. The method of claim 1, wherein the method comprises obtaining biological samples from the patients and performing a genetic assay to determine the presence or absence of allele HLA-B*39:01 in the biological samples.

4. The method of claim 3, comprising obtaining PCR-amplified genomic DNA samples of the biological samples from the patients, contacting under hybridizing conditions the genomic DNA with an oligonucleotide that specifically hybridizes to HLA-B*39:01, and detecting the presence or absence of HLA-B*39:01 in the samples.

5. The method of claim 1, wherein the infliximab is administered to a patient in the population at a dose of at least 5 mg/kg infliximab.

6. The method of claim 1, wherein the infliximab is administered to a patient in the population at a dose of about 5 mg/kg to about 10 mg/kg infliximab.

7. The method of claim 1, wherein the infliximab is administered to a patient in the population at a dose of about 5 mg/kg infliximab.

8. The method of claim 1, wherein the autoimmune disease is selected from the group consisting of Crohn's disease, ulcerative colitis, rheumatoid arthritis, ankylosing spondylitis, psoriatic arthritis, and plaque psoriasis.

9. The method of claim 1, wherein the autoimmune disease therapy that is not infliximab is a TNF inhibitor.

10. The method of claim 1, wherein the autoimmune disease therapy that is not infliximab is selected from the group consisting of azathioprine, mercaptopurine, adalimumab, certolizumab, methotrexate, natalizumab, vedolizumab, ustekinumab, mesalamine, budesonide, hyoscyamine, celecoxib, hydroxychloroquin, etanercept, prednisone, cyclosporine, tocilizumab, meloxicam, leflunomide, sulfasalazine, abatacept, rituximab, golimumab, acitretin, secukinumab, apremilast, sarilumab, ixekizumab, and corticotropin.

* * * * *